(12) United States Patent
Farrar et al.

(10) Patent No.: US 6,916,846 B2
(45) Date of Patent: Jul. 12, 2005

(54) COUMERMYCIN ANALOGS AS CHEMICAL DIMERIZERS OF CHIMERIC PROTEINS

(75) Inventors: Michael A. Farrar, Minneapolis, MN (US); Steven H. Olson, Metuchen, NJ (US); Roger M. Perlmutter, Seattle, WA (US); Llnon H. Slossberg, News Brunswick, NJ (US)

(73) Assignee: Merck & Co. Inc., Rahway, NJ (US)

( * ) Notice: Subject to any disclaimer, the term of this patent is extended or adjusted under 35 U.S.C. 154(b) by 650 days.

(21) Appl. No.: 09/840,260

(22) Filed: Apr. 23, 2001

(65) Prior Publication Data

US 2002/0095026 A1 Jul. 18, 2002

Related U.S. Application Data

(60) Provisional application No. 60/203,656, filed on May 12, 2000.

(51) Int. Cl.[7] .............................................. A01N 43/16
(52) U.S. Cl. ..................... 514/457; 548/530; 514/427
(58) Field of Search ................................ 514/457, 427; 548/530

(56) References Cited

U.S. PATENT DOCUMENTS

| 3,627,886 A | 12/1971 | Newmark ................. 424/181 |
| 5,830,462 A | 11/1998 | Crabtree et al. ......... 424/93.21 |
| 5,834,266 A | 11/1998 | Crabtree et al. ............ 435/456 |

FOREIGN PATENT DOCUMENTS

WO     WO 99/35155     7/1999

OTHER PUBLICATIONS

M. A. Farrar et al., Activation of the Raf-1 Kinase Cascade by Coumermycin Induced Dimerization, Nature, vol. 383, pp. 178–181, Sep. 12, 1996.
T. P. Curran et al., J. Org. Chem., vol. 61, p. 9068, 1996.
P. Laurin et al., Bioorg. Med. Chem. Lett., vol. 9, p. 2079, 1999.

Primary Examiner—David Lukton
(74) Attorney, Agent, or Firm—Sylvia A. Ayler; Valerie J. Camara

(57) ABSTRACT

Coumermycin analogs of general formula I:

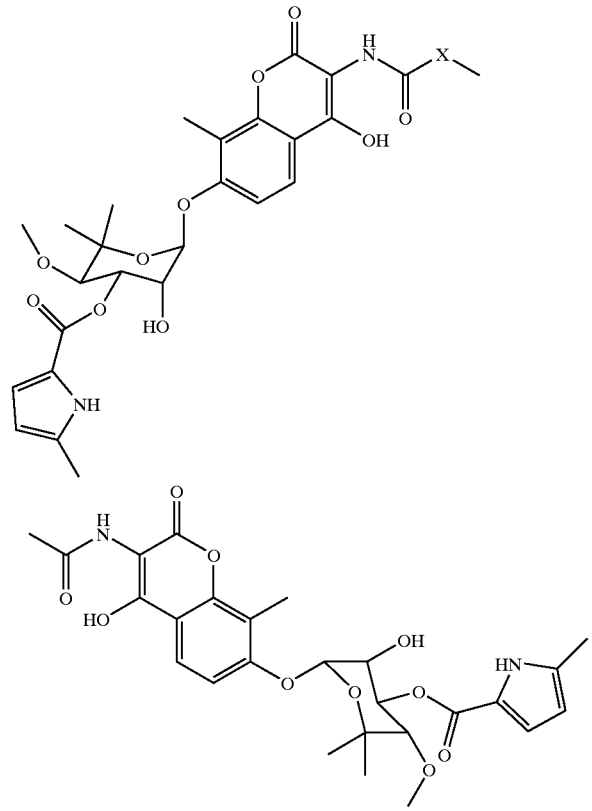

wherein X, a linking group, is selected from the group consisting of alkyl, aryl, diaryl, substituted alkyl, substituted aryl, alkyl with hereroatoms in the chain, heteroaryl, cyclic and bicyclic alkyl, and a combination of alkyl, aryl and heteroaryl substituents. The compounds are suitable for use as chemical dimerizers of chimeric proteins.

26 Claims, No Drawings

COUMERMYCIN ANALOGS AS CHEMICAL DIMERIZERS OF CHIMERIC PROTEINS

This application claims the benefit of provisional application 60/203,656, filed May 12, 2000.

FIELD OF THE INVENTION

The present invention is directed to coumermycin derivatives useful for promoting the dimerization of chimeric signaling, intracellular proteins.

BACKGROUND OF THE INVENTION

Signal transduction is the process by which extracellular molecules influence intracellular events. A cellular response generally involves multiple signal transduction cascades that operate in concert to elicit a specific biological response. Activities of signal transduction pathways can be regulated through the use of biological molecules, i.e. protein kinases. While many of the proteins in these pathways are known, little is understood about the relationship between particular signal transduction pathways.

In U.S. Pat. No. 5,830,462, issued Nov. 3, 1998; and U.S. Pat. No. 5,834,266, issued Nov. 10, 1998, both to Crabtree et al (both incorporated herein by reference hereto), a general procedure for the regulation of dimerization and oligomerization of intracellular proteins as biological, control mechanisms is suggested. Crabtree further teaches that many signaling pathways originate with the binding of extracellular ligands to cell surface receptors, and receptor dimerization can lead to transphosphorylation and the recruitment of proteins that continue the signal transduction cascade.

In "Activation of the Raf-1 Kinase Cascade by Coumermycin Induced Dimerization," Farrar, M. A., Alberola-Ila, J. and Perlmutter, R. M., Nature, Vol. 383, pp. 178–181, Sep. 12, 1996 (incorporated herein by reference hereto), the carboxy terminus of Raf-1 serine/threonine kinase was covalently attached to the amino terminus of the B subunit of bacterial DNA gyrase (GyrB). *Streptomyces* derived natural products, coumermycin and novobiocin, are known to bind GyrB with strong affinity. The region that binds the protein is known to be an oligosaccharide (also known as noviose sugar) and the attached coumarin, a common element between the 2 structures. The stoichiometry of binding between GyrB and drug is 2:1 for coumermycin and 1:1 for novobiocin.

Farrar et al suggests adding coumermycin to the chimeric Raf-GyrB fusion protein wherein, coumermycin bound 2 molecules of GyrB that concomitantly brought the 2 Raf kinases into close proximity to one another. This close proximity induced Raf dimerization and led to activation of the Raf kinase cascade.

Furthermore, Farrar et al teaches that if a sufficient concentration of novobiocin is added to the coumermycin/GyrB/Raf complex, coumermycin can be displaced from the GyrB active site having similar binding constants and block kinase activation.

Coumermycin is known to have induced dimerization of the tyrosine kinase, Jak2, as well as the transcription factors STAT3, STAT5a, and STAT5b. Unfortunately, it has failed to activate a number of other proteins involved in signal transduction. It is believed that GyrB-Coumermycin-GyrB complex can not orient all kinases and transcript factors into the proper orientation for cross-phosphorylation. A coumermycin analog with a more flexible or longer spacing group will result in the activation of additional signaling proteins, and might have enhanced cellular penetration and potency than coumermycin.

SUMMARY OF THE INVENTION

The present invention is directed to coumermycin analogs of general formula I:

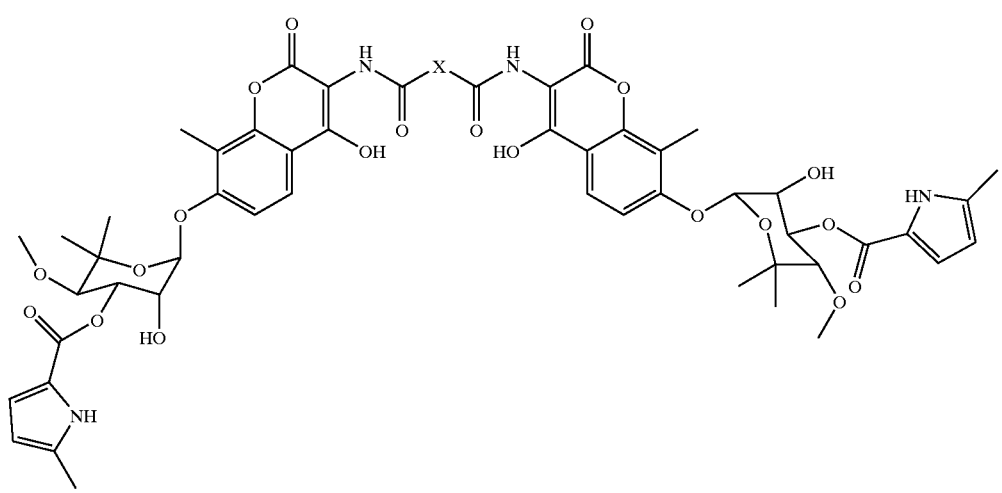

or a pharmaceutically acceptable salt or ester thereof, wherein X is a linking group that connects the two halves of the molecule.

DETAILED DESCRIPTION OF THE INVENTION

The present invention is described herein in detail using the terms defined below unless otherwise specified.

As used herein the term "alkyl" refers to a monovalent alkane (hydrocarbon) derived radical containing from 1 to 18 carbon atoms. It can be straight, branched, or cyclic. Preferred alkyl groups include methyl, ethyl, propyl, isopropyl, butyl, t-butyl, cyclopentyl and cyclohexyl. When the alkyl group is said to be substituted with an alkyl group, this is used interchangeably with "branched alkyl group".

The term "aryl" refers to aromatic rings, e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "diaryl" refers to two aromatic rings linked together.

The phrase "alkyl with heteroatoms in the chain" refers to alkyl substituents having one or more altered or continuing oxygen, sulfur or nitrogen atom in the chain replacing carbon atoms.

The term "cyclic alkyl" or "cycloalkyl" refers to a specie of alkyl containing from 3 to 18 carbon atoms, without alternating or resonating double bonds between carbon atoms. It may contain from 1 to 4 rings which are fused. Preferred cyclic alkyls are organic substituents having only one ring structure containing alkyl groups therein or having two fused, cyclic ring structures containing alkyl groups therein.

The phrase "combination of alkyl, aryl and heteroaryl" refers to substituents that contain various at least two of the referenced substituents in combination.

The term "heteroatoms" refers to O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms are optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

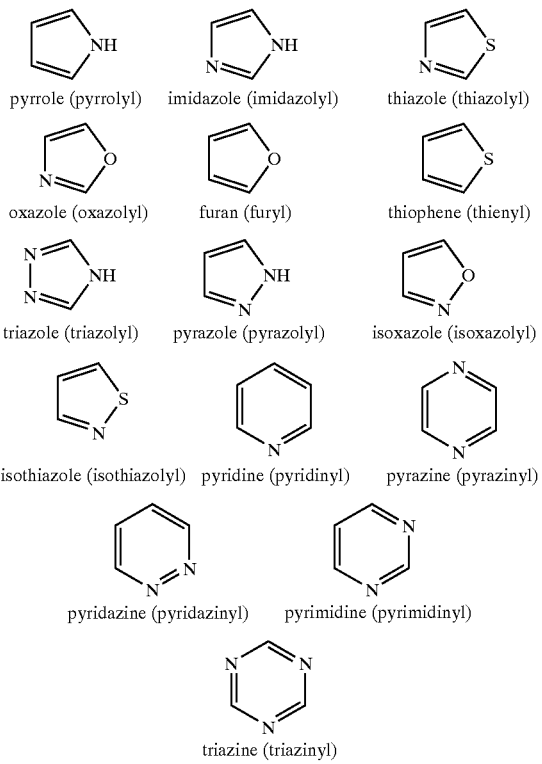

The present invention is directed to coumermycin analogs, pharmaceutically-acceptable esters and salts thereof of general formula I:

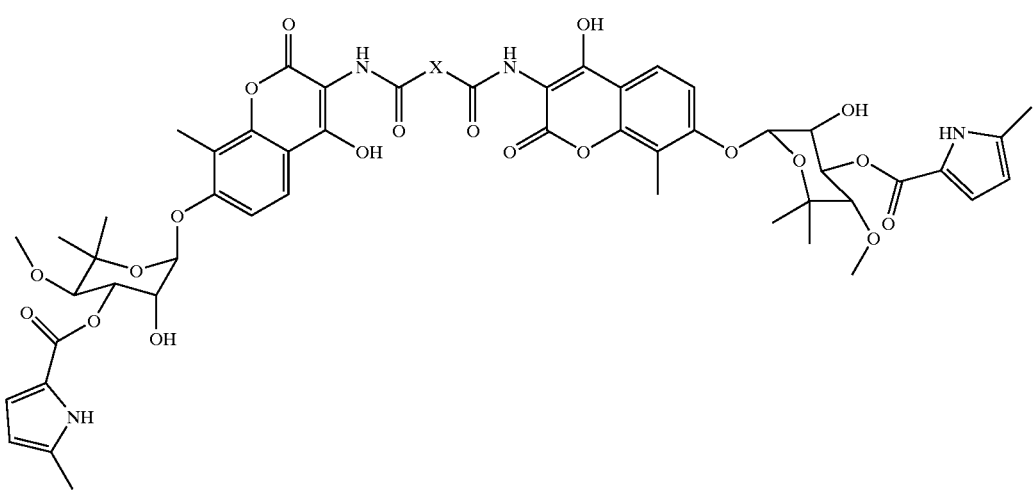

I wherein X, a linking group that connects the two halves of the molecule may contain from about 1 to about 54 atoms. The linking group, X, may be selected from alkyl, aryl, diaryl, substituted alkyl, substituted aryl, diaryl, substituted alkyl, alkyl with hereroatoms in the chain, heteroaryl, cyclic and bicyclic alkyl, and a combination of alkyl, aryl and heteroaryl substituents. Optionally, the linking group may also be selected from pyrrole, pyridine, furan, indole, benzofuran, dibenzofuran, thiophene, straight chain alkyl, cycloalkyl, phenyl, diaryl, derivatives and combinations thereof. The pyrrole moiety may be selected from the following:

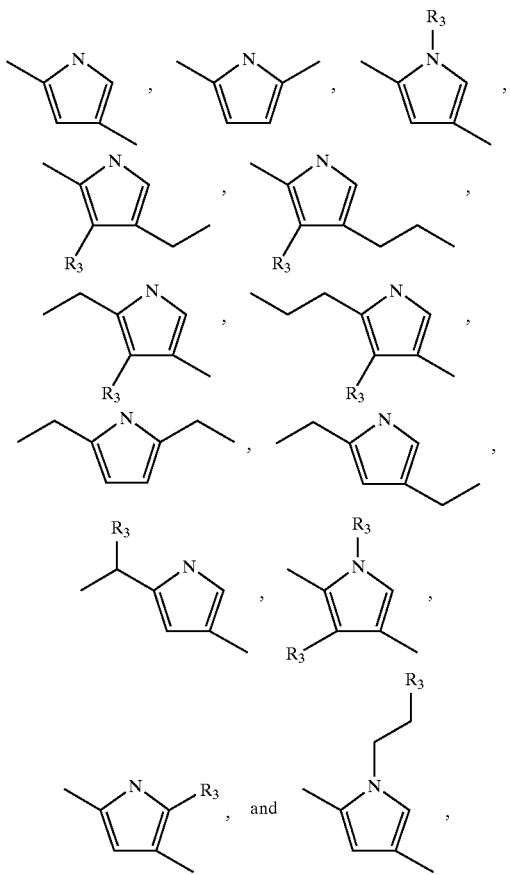

wherein $R_3$ is H or $CH_3$.

The diaryl moiety may be selected from the following:

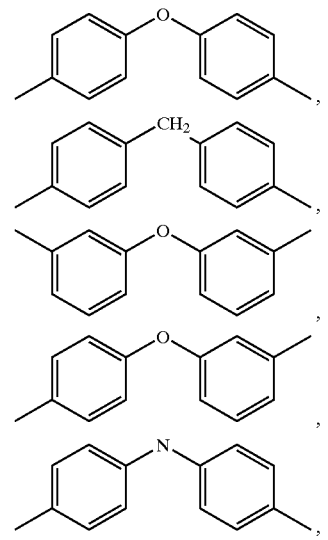

-continued

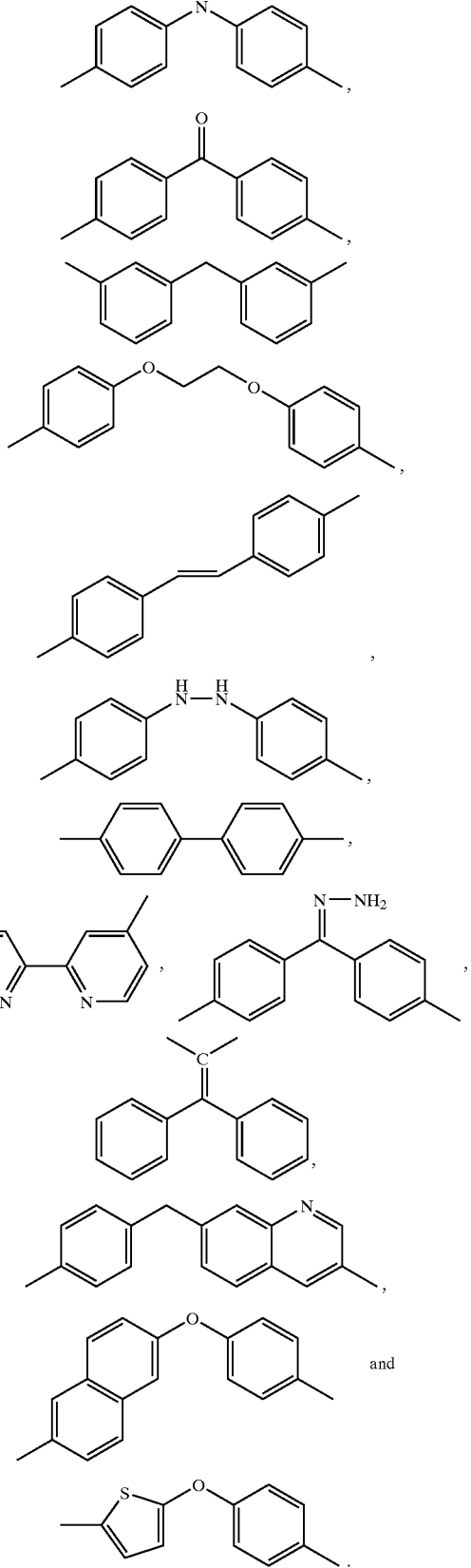

The pyridine moiety may be selected from the following:
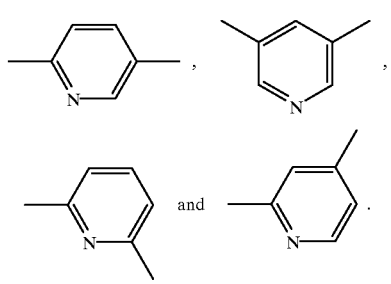
The straight alkyl chain may contain from about 1 to about 18 carbon atoms therein.
The indole moiety may be selected from the following:
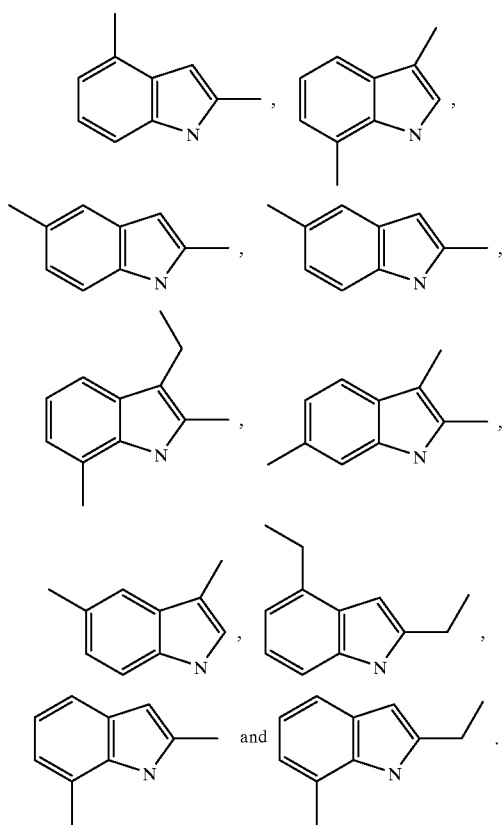
The benzofuran moiety may be selected from the following:
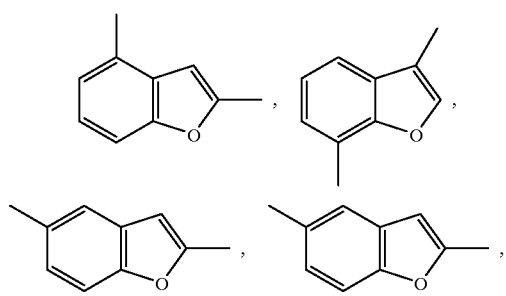
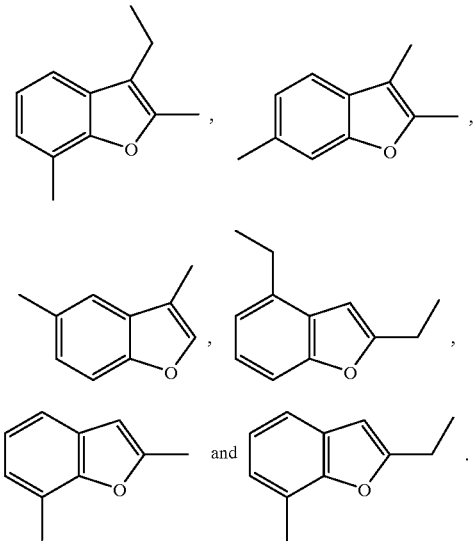
The phenyl moiety may be selected from the following:
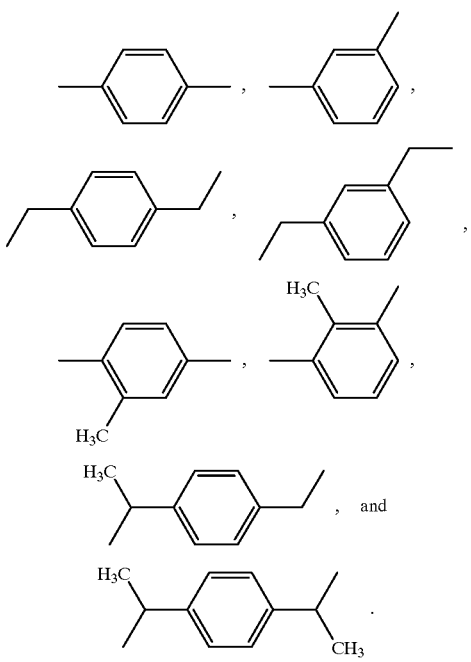
The cycloalkyl moiety may be selected from the following:
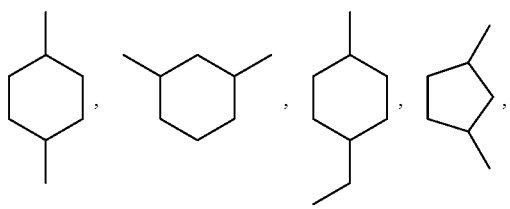

-continued

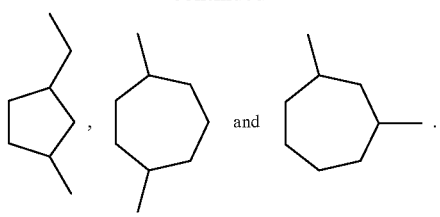

The furanyl moiety may be selected from the following:

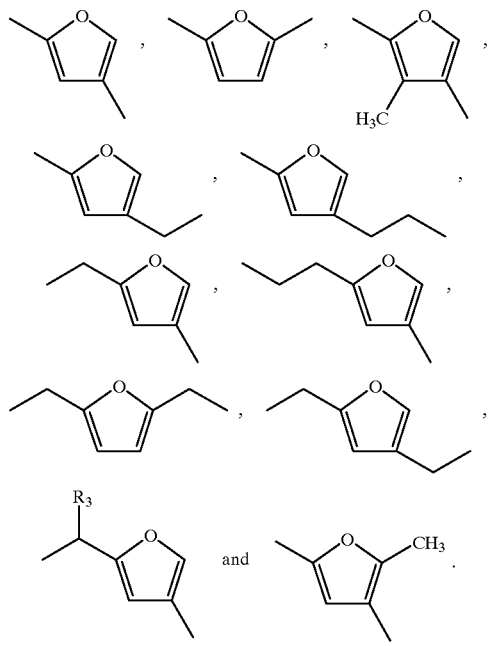

The dibenzofuranyl moiety may be selected from the following:

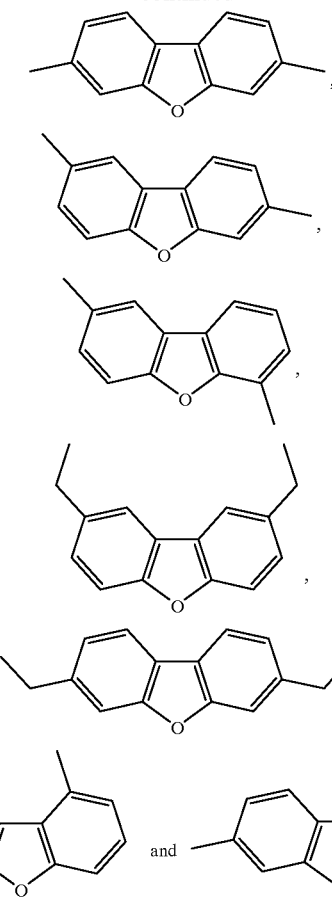

The analogs are suitable for use as chemical dimerizers oligomerizers of chimeric proteins.

The coumermycin analogs of the present invention are useful as chemical dimerizers of chimeric protein kinases or transcription factors. The analogs are capable of covalently attaching the carboxy terminus of Raf-1 serine/threonine kinase to the amino terminus of the B subunit of bacterial DNA gyrase (GyrB).

Coumermycin is a natural product known to be useful in the inhibition of amino-terminal 24K subdomain of the B subunit of bacterial DNA gyrase (GyrB).

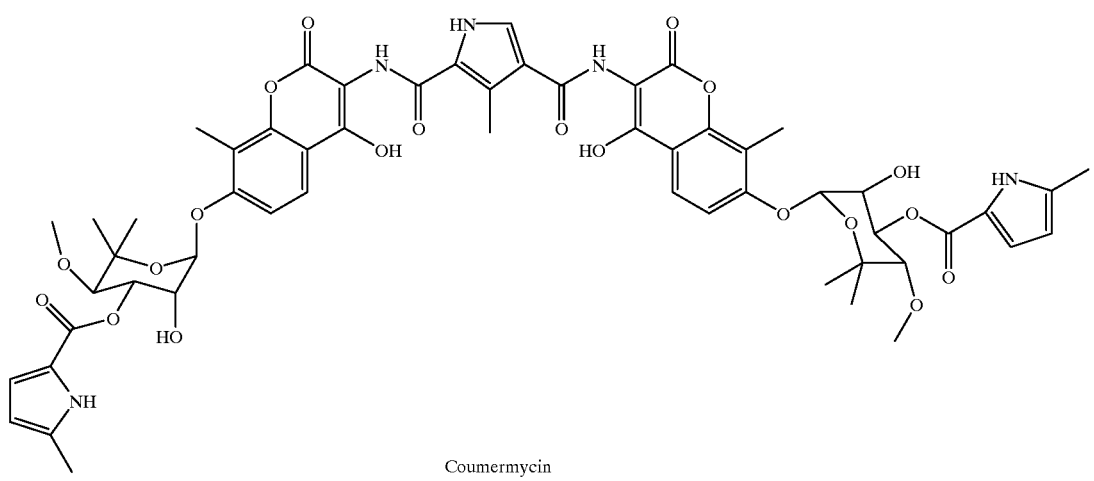

Coumermycin

Analogs of coumermycin may be prepared in accordance with the chemical synthesis sequence from commercially available materials, as presented herein.

In the present invention, organic molecules regulate signal transduction pathways by activities, among others, proteins or transcription factors. A natural molecule, coumermycin, simultaneously binds two (2) molecules of a B subunit of bacterial DNA gyrase (GyrB) which are, in turn, covalently linked to Raf-1 kinase. The binding event brings the 2 chimeric proteins in close proximity to one another and promotes dimerization (or phosphorylation) of the 2 Raf-1 enzymes which activates a signal transduction pathway. A monomeric natural product, novobiocin, binds just one of these GyrB-Raf-1 chimers and prevents (or turns off) the signaling cascade. Unfortunately the coumermycin/GyrB system can activate only a select few kinase systems. It is, therefore necessary to prepare coumermycin analogs that will induce cross-phosphorylation in a more general manner.

The present invention is further directed to a method of chemically dimerizing chimeric proteins utilizing a coumermycin analog of general formula I:

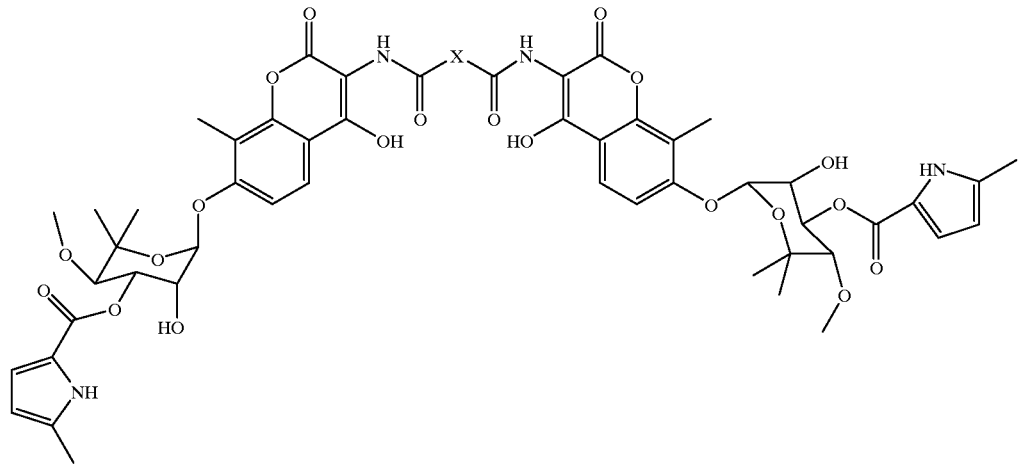

wherein X is a linking group selected from straight, branched and cyclic alkyl, aryl, diaryl, substituted aryl, diaryl, substituted alkyl, alkyl with heteroatoms in the chain, heteroaryl, a combination of alkyl, aryl, heteroaryl, pyridine, furan, indole, benzofuran, dibenzofuran, thiophene, straight chain alkyl, cycloalkyl, phenyl, diaryl and combinations thereof.

Examples of coumermycin analogs may be selected from the following

| Compound No. | Structure |
|---|---|
| 1 | 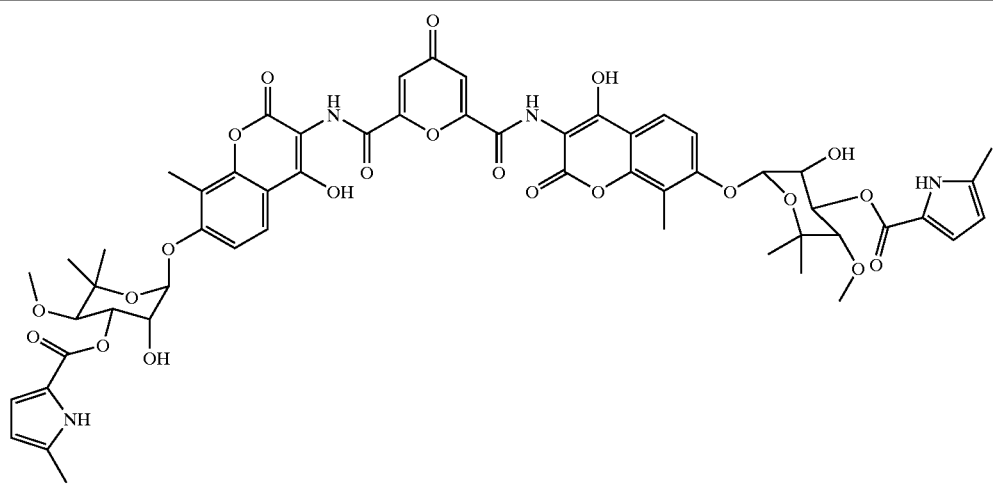 |

-continued

| Compound No. | Structure |
|---|---|
| 2 | 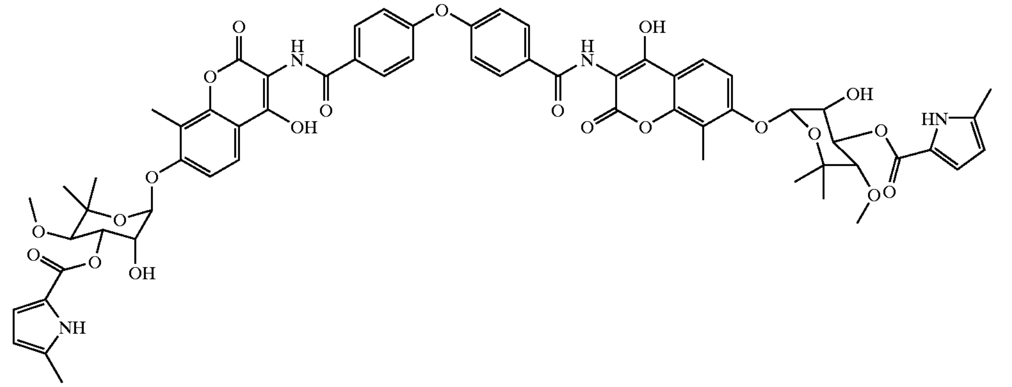 |
| 3 | 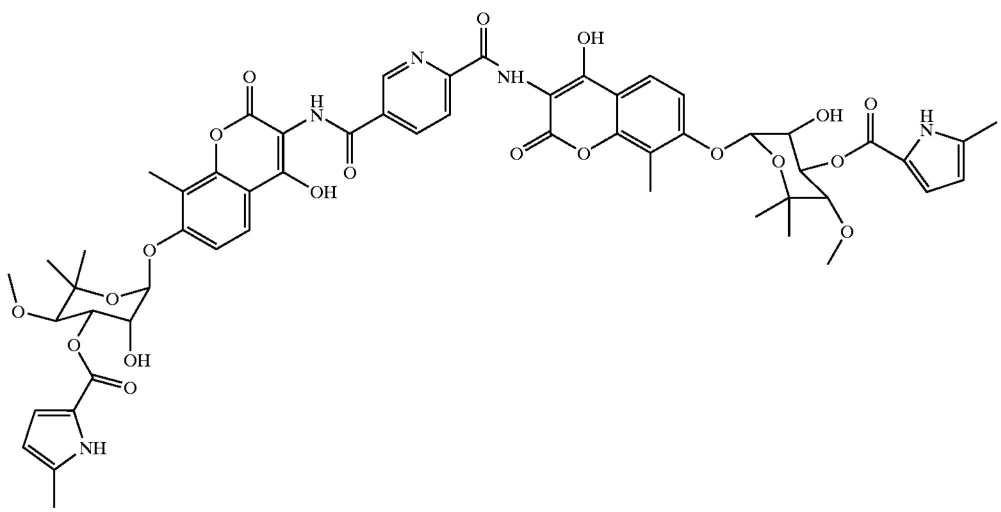 |
| 4 | 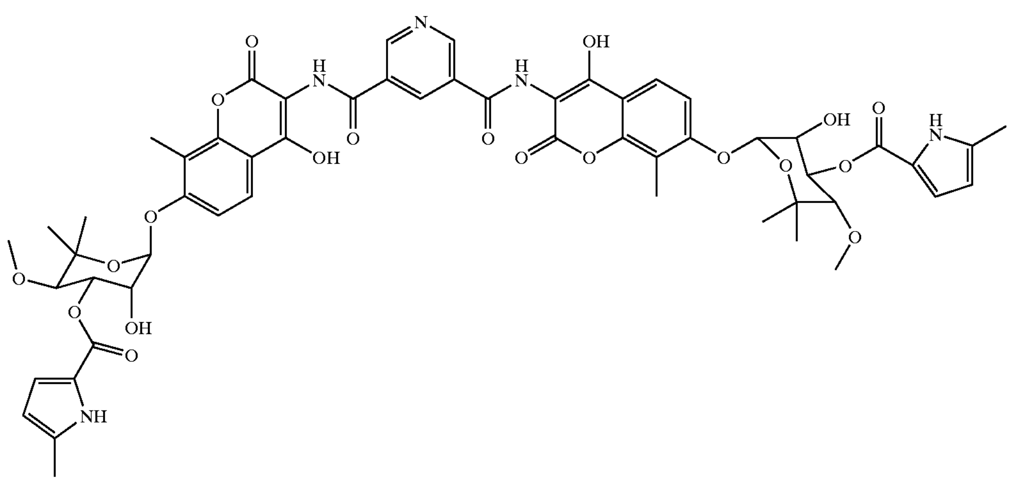 |

| Compound No. | Structure |
|---|---|
| 5 | 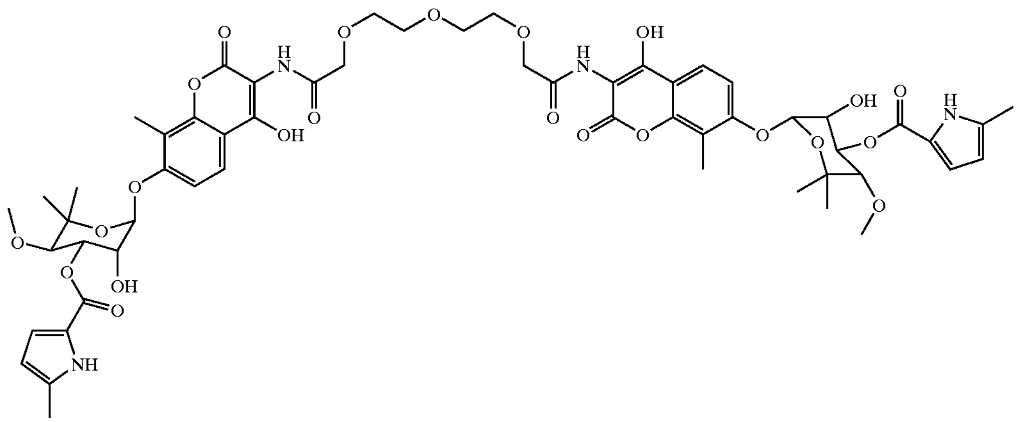 |
| 6 | 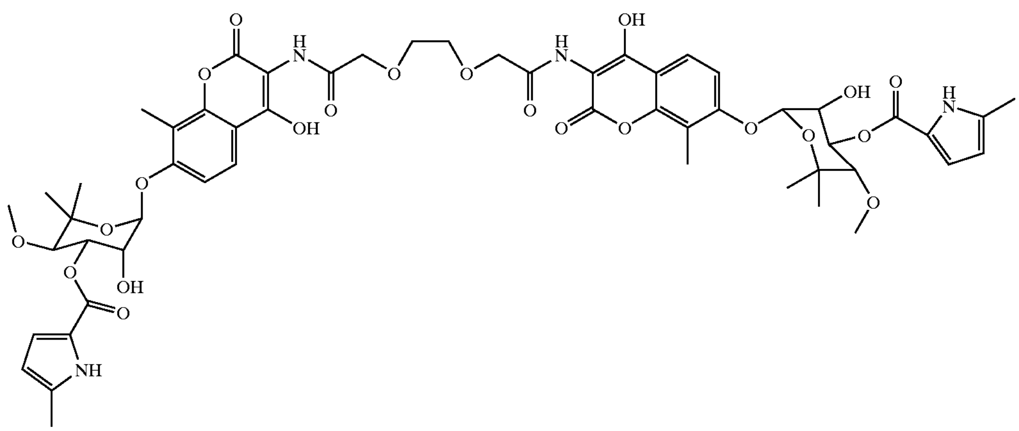 |
| 7 | 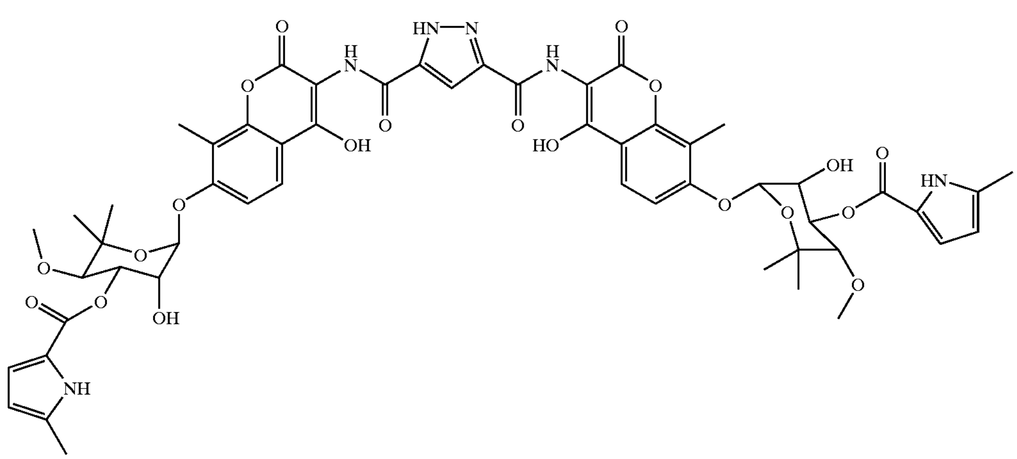 |

| Compound No. | Structure |
|---|---|
| 8 | 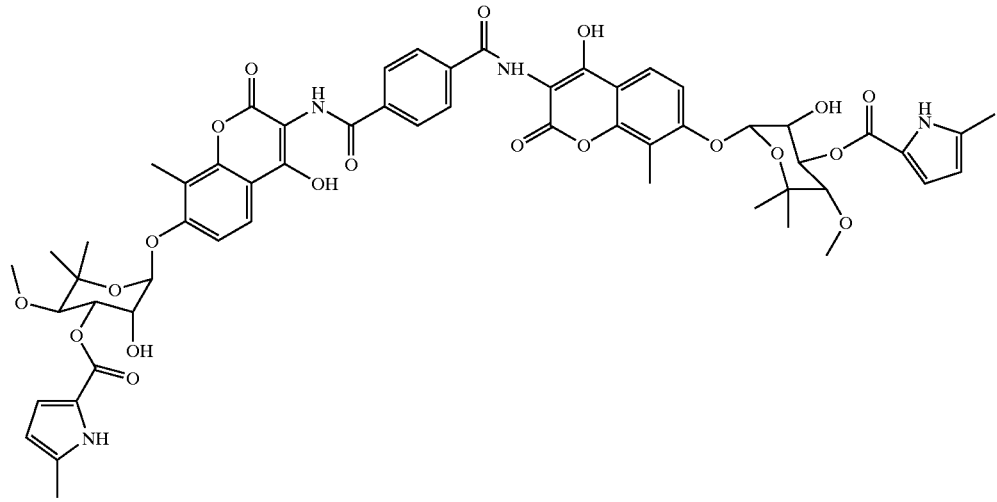 |
| 9 | 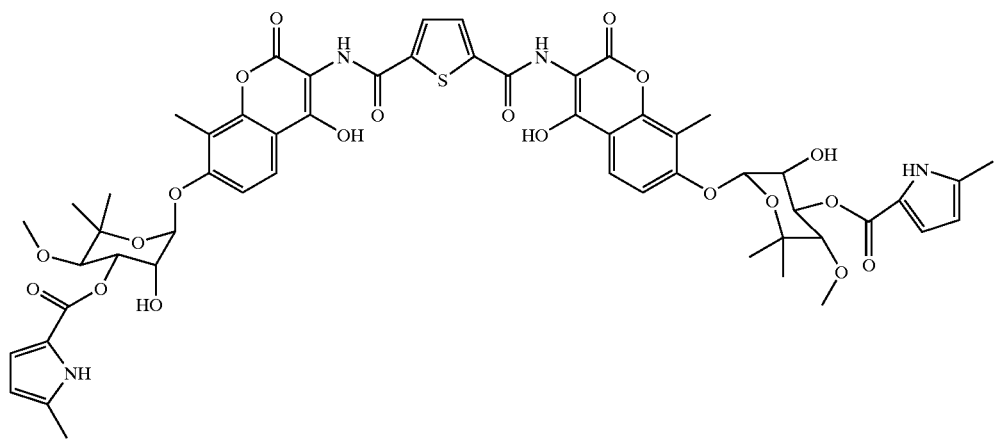 |
| 10 | 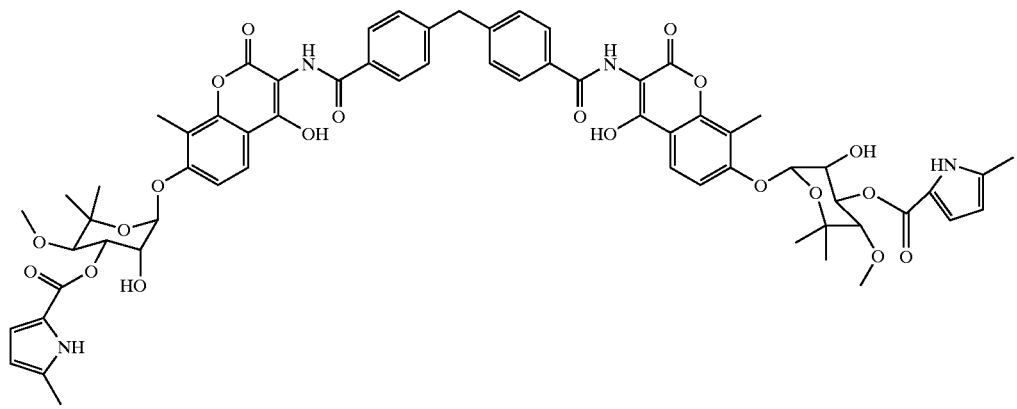 |

| Compound No. | Structure |
|---|---|
| 11 | 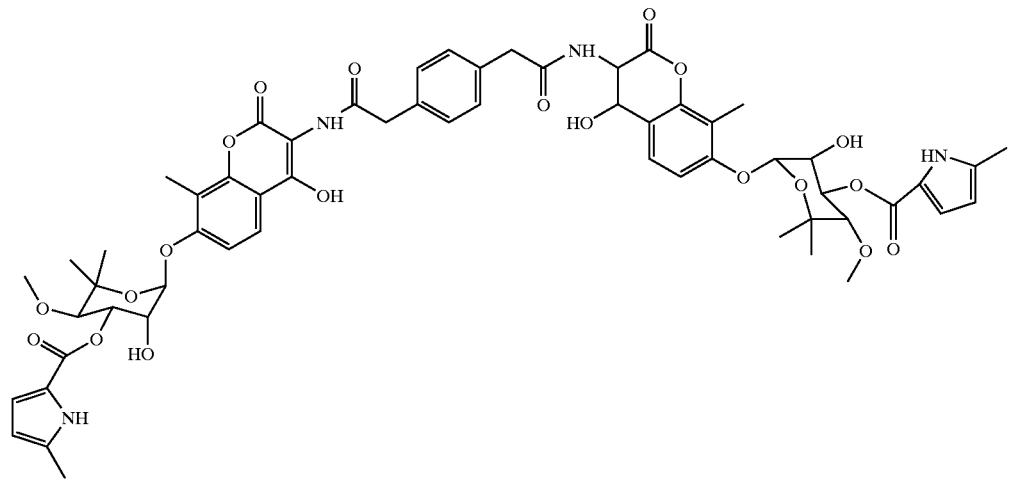 |
| 12 | 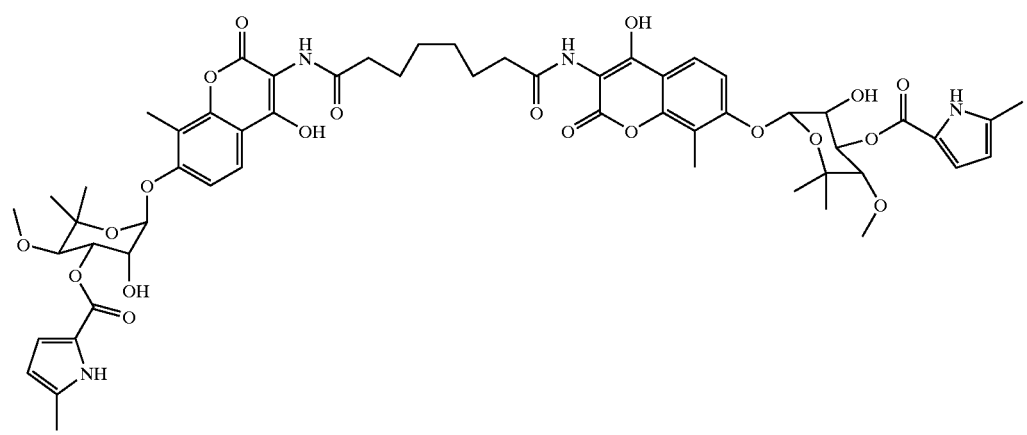 |
Synthesis Schemes
The compounds of this invention can be synthesized by methods known in the art. As illustrated herein, the compounds can be synthesized in accordance with Synthesis Schemes I through V.
Those skilled in the art will appreciate other methods thereof after reviewing the following:

SCHEME I
Synthesis of the Noviose Fragment

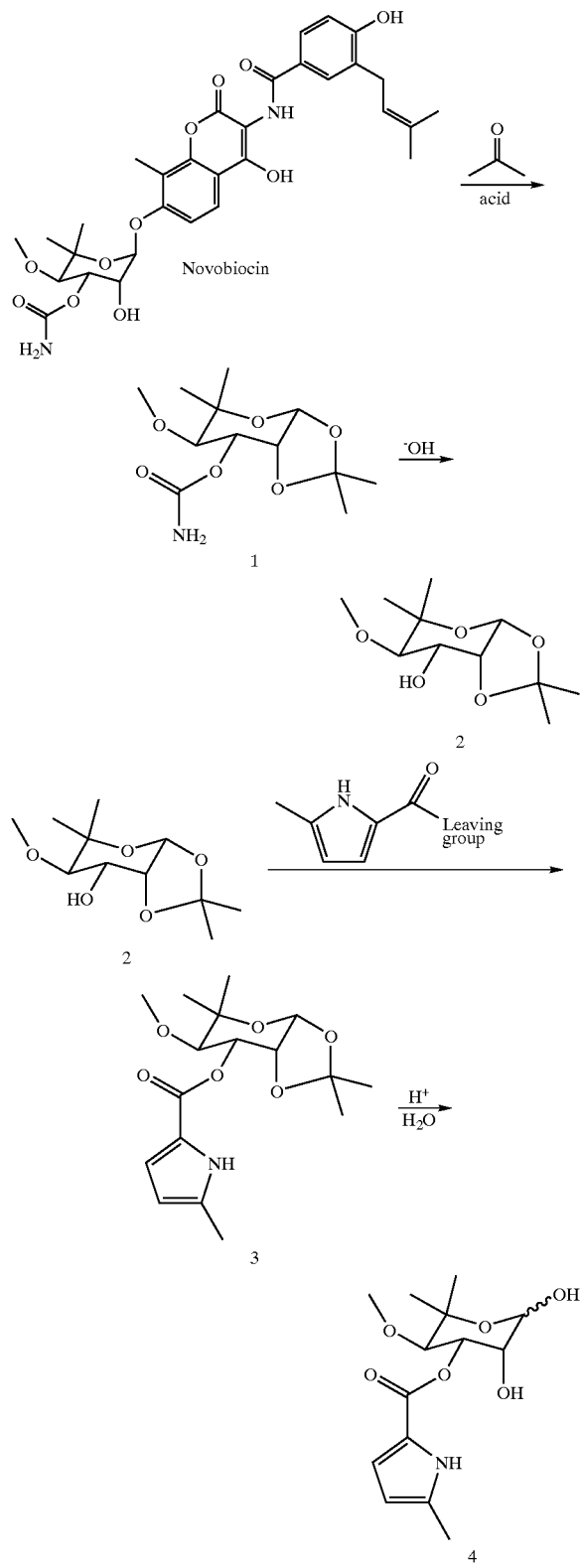

A protected version of the noviose sugar (1) is prepared by exposing commercially available novobiocin to a Lewis acid or protic acid, preferably a strong protic acid, more preferably toluenesulfonic acid in the presence of acetone. Hydrolysis of the C-3' carbamate moiety is accomplished by stirring with hydroxide, preferably lithium hydroxide, to give 2. The C-3' position of the sugar was acylated by exposing 2 to a derivative of 5-methyl pyrrole-2-carboxylic acid where the carboxylic acid is activated for acylation. Preferably the pyrrole is activated as an anhydride (see compound 7 in Scheme II) and preferably an acylation catalyst is used, more preferably the acylation catalyst is tributyl phosphine. Protected sugar 3 is converted to the reducing sugar 4 by exposure to acid, preferably trifluoroacetic acid.

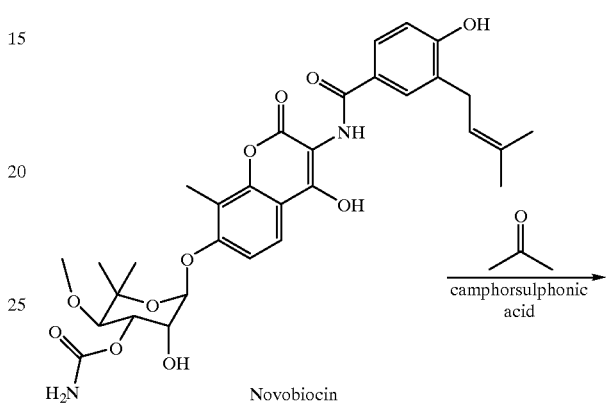

A stirring mixture of novobiocin (12.0 g), p-toluenesulfonic acid (3.6 g) in 100 mL anhydrous acetone was heated to 48° C. A white precipitate formed during course of the reaction. After six hours, the cloudy white solution was cooled to room temperature and the acetone was removed in vacuo. The resulting solid was purified by column chromatography (basic alumina, 100% ethyl acetate) to give 3.2 g of the protected noviose sugar 1. Mass spectra (MS) (ESI) m/z= 298 (M+Na⁺).

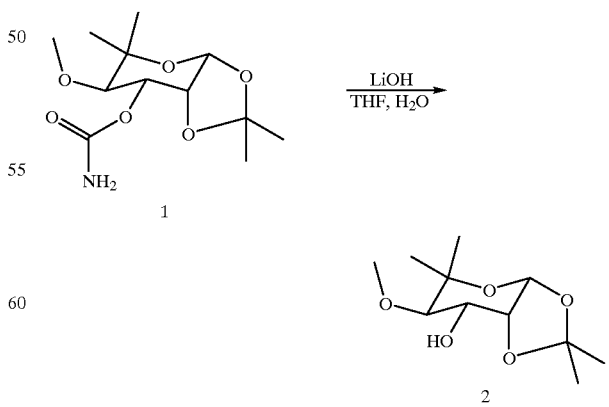

Sugar acetonide 1 (2.5 g) was dissolved in 30 mL methanol and 30 mL THF (tetrahydrofuran). Lithium hydroxide hydrate (2.9 g) was dissolved in 30 ml of water and added to the stirring solution. The solution was warmed to 40° C. and stirred overnight. The product 2 was extracted with water and ethyl acetate (3×). No purification was necessary. MS (ESI) m/z=255 (M+Na⁺).

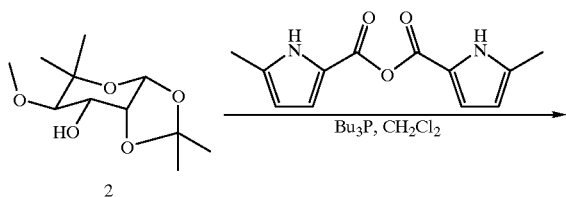

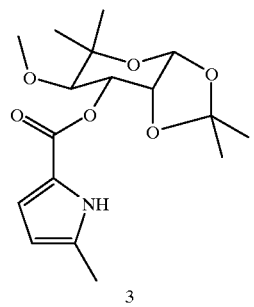

Noviose sugar (0.82 g) 2 and pyrrole anhydride 7 (1.6 g) were dissolved in 50 mL of dry methylene chloride and stirred at room temperature under nitrogen.
Tributylphosphine (0.77 g) was added and the solution was stirred for 60 hours. The solution was added to 30 mL water and extracted twice with methylene chloride. The organic layers were combined, dried over magnesium sulfate, filtered, and dried in vacuo. The crude sugar was purified by silica gel chromatography (20%→25%→33% ethyl acetate in hexane) to provide the acylated noviose 3 (0.99 g). MS (ESI) m/z=362 (M+Na⁺).

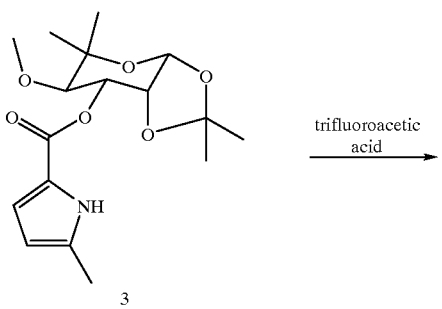

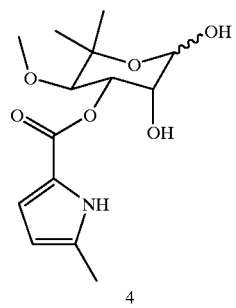

The protected noviose (513 mg) was dissolved in a 4:1 mixture of trifluoroacetic acid (TFA):water (5 mL) and stirred at room temperature for five minutes. The solvents were removed in vacuo and the resulting solid was filtered through silica gel (100% ethyl acetate). The purified reducing sugar 4 was obtained as a mixture of anomers (381 mg). MS (ESI) m/z=322 (M+Na⁺).

SCHEME II
Synthesis of the Acyl Pyrrole Fragment

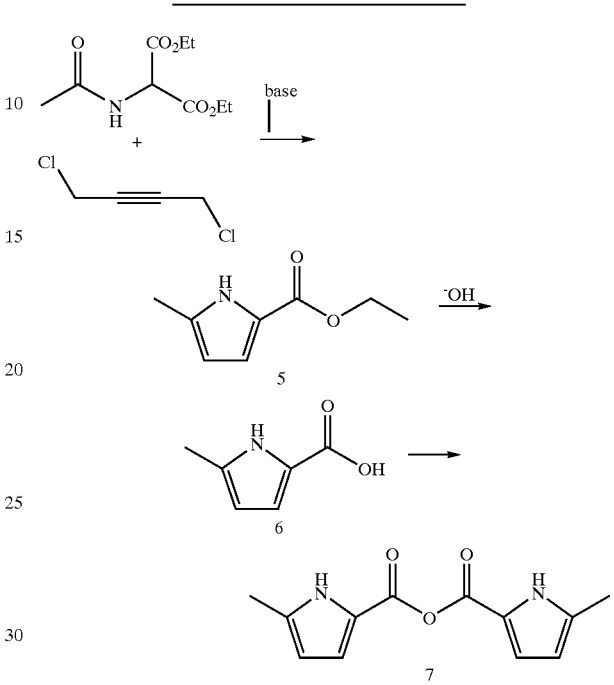

Syntheses of 5-methylpyrrole-2-carboxylic acid and its derivatives are well known in the literature. We found the method of Curran, T. P., Keaney, M. T. *J. Org. Chem.* 61, 9068 (1996) to be preferred. Mixing ethyl acetamidomalonate and 1,4-dichloro-2-butyne in the presence of base, preferably sodium ethoxide, provided pyrrole ester 5. Hydrolysis in the presence of hydroxide, preferably lithium hydroxide gave the desired carboxylic acid 6. Activation of the carboxylic acid 6 was accomplished by exposing the carboxylic acid to a peptide coupling reagent, preferably a carbodiimide, more preferably 1-(3-dimethylaminopropyl)-3-ethylcarbodiimide hydrochloride. The anhydride product 7 can be used in Scheme I to acylate the noviose sugar fragment 2.

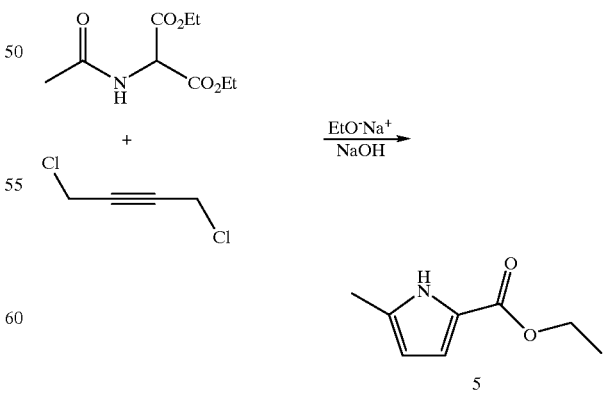

The procedure of Curran, T. P., Keaney, M. T. *J. Org. Chem.* 61, 9068 (1996) was followed. Diethyl acetamidomalonate (0.395 g) was added to a solution of sodium ethoxide in ethanol (1.0 M, 9 mL) and the solution was heated to reflux (95° C. to 97° C.). 1,4-dichloro-2-butyne (190 µL) was added and the solution was refluxed for one hour. Additional portions of 1,4-dichloro-2-butyne (190 µL) and sodium ethoxide in ethanol (0.70 mL, 21 wt. %) were added and heating continued for another hour. When complete, the solution was cooled to room temperature and the ethanol was removed in vacuo. The brown residue was dissolved in ethyl acetate and extracted water (2×), saturated sodium bicarbonate (3×), 1N HCl (3×), and brine. The organic layer was dried over magnesium sulfate, filtered and evaporated. The resulting solid was purified by column chromatography (silica gel, 10% ethyl acetate in hexane) to give 130 mg of the ethyl ester 5. MS (ESI) m/z=154 (M+H$^+$).

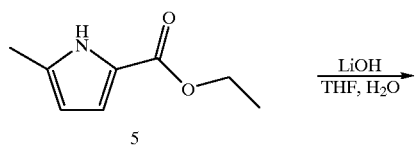

The ethyl ester 5 (4.5 g) was dissolved in methanol (50 mL) and THF (50 mL). Lithium hydroxide hydrate (10.0 g) was dissolved in water (50 mL) and added to the stirring solution. The reaction was stirred overnight at 40° C. The crude product was added to dilute aqueous HCl (pH between 1.5–3.0) and extracted with ethyl acetate (3×). The organic layers were combined, dried over magnesium sulfate, and filtered and evaporated to give 6 (3.6 g). No purification was necessary.

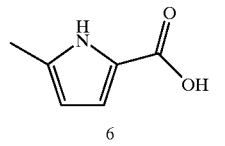

5-methyl-pyrrole-2-carboxylic acid 6 (4.8 g) was dissolved in methylene chloride (150 mL) and stirred at room temperature under nitrogen. 4-methylmorpholine (2.11 mL) was added followed by 1-(3-dimethylaminopropyl)-3-ethylcarbodiimide hydrochloride (3.68 g). After stirring for two hours, the crude material was added to water and extracted with methylene chloride (3×). The organic layers were combined, dried over magnesium sulfate, filtered, and dried in vacuo. The product was purified by column chromatography (silica gel, 33% ethyl acetate/67% hexane) and provided the desired anhydride 7 (3.65 g). MS (ESI) m/z= 233 (M+H$^+$).

SCHEME III

Synthesis of the Coumarin Fragment

A number of literature procedures exist for the synthesis of the coumarin core of coumermycin. The method of Laurin, P. et al., *Bioorg. Med. Chem Lett.* 9, 2079 (1999) and Haesslein, J-L. et al. WO 99/35155 is preferred. Commercially available 2,4-dihydroxy-3-methylacetophenone was selectively protected with dihydropyran is the presence of acid, preferably toluenesulfonic acid, to provide 8. The coumarin fragment 9 was prepared by exposure to an appropriate electrophile, preferably diethyl carbonate, to in the presence of base. Protection of 9 was accomplished addition of diphenyl diazomethane to form 10. Removal of the tetrahydropyranyl protecting group occurred in the presence of water under acid catalysis to yield compound 11.

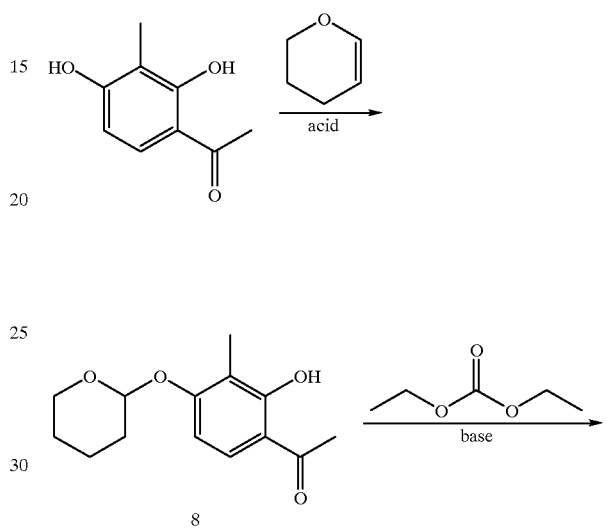

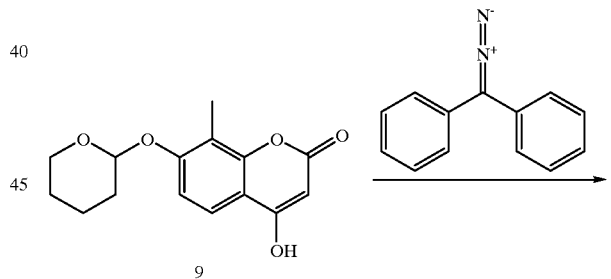

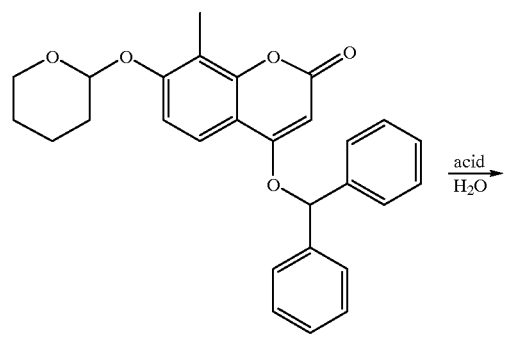

-continued

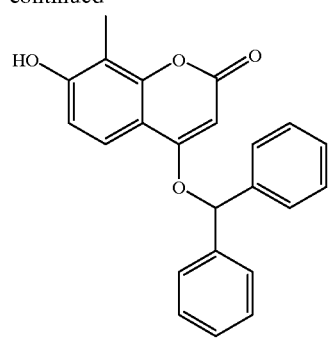

11

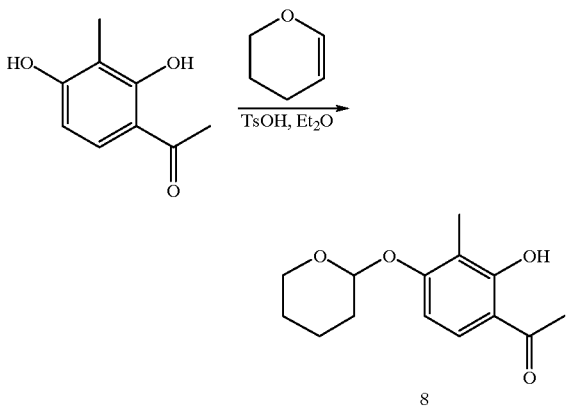

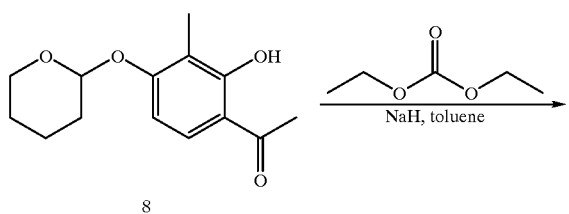

8

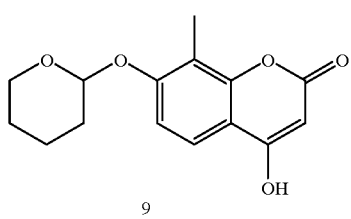

9

The procedure of Laurin, P. et al., *Bioorg. Med. Chem Lett.* 9, 2079 (1999) was followed. Protected acetophenone 8 (15.9 g) was dissolved in toluene (170 mL). Diethyl carbonate was added and the solution was heated to 90° C. under nitrogen with vigorous stirring. Sodium hydride (60% in mineral oil, 5.87 g) was added portionwise to prevent foaming. Stirred at 90° C. overnight. Cooled to room temperature and an off-white solid was collected after centrifugation. The solid was triturated with ether, 1M $NaH_2PO_4$, water, acetone, and ether again and the resulting sodium salt of the coumarin was collected as a white solid. The coumarin was dissolved in methanol and acidified with acetic acid. Water was added and the methanol was removed in vacuo. The white precipitate was collected by filtration and dried to give the desired coumarin 9. MS (ESI) m/z=277 (M+H$^+$)

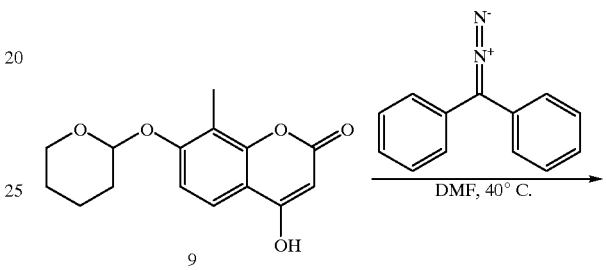

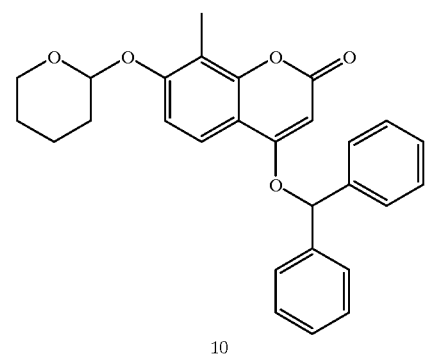

10

The procedure of Laurin, P. et al., *Bioorg. Med. Chem Lett.* 9, 2079 (1999) was followed. Anhydrous diethyl ether (130 mL) was added to 2,4-dihydroxy-3-methylacetophenone (21.52 g). The mixture was stirred under nitrogen and dihydropyran (21.5 mL) was added. The mixture was cooled to 0° C. Toluenesulfonic acid (118 mg) was added and the reaction was allowed to slowly warm to room temperature. After twelve hours another portion of toluenesulfonic acid (80 mg) was added. The black solution was stirred an additional six hours and then added to a saturated sodium bicarbonate solution. Extraction with ether followed by drying over magnesium sulfate, filtration and solvent removal provided a black solid which was purified by column chromatography (Silica gel, 20%→25%→33% ethyl acetate in hexane) to provide the protected acetophenone 8 (15.9 g). MS (ESI) m/z=251 (M+H$^+$)

The procedure of Laurin, P. et al., *Bioorg. Med. Chem Lett.* 9, 2079 (1999) was followed. The coumarin 9 (2.85 g) was dissolved in dimethyl formamide (DMF) (13 mL) and warmed to 90° C. under nitrogen. Diphenyl diazomethane (3 g) was dissolved in DMF (13 mL) and added dropwise to the reaction mixture over 150 minutes. After two hours additional diphenyl diazomethane (400 mg) was added. After two more hours diphenyl diazomethane (400 mg) was added again. Stirred an additional 6 hours at 90° C. The solution was cooled to room temperature and added to water. After extraction with ethyl acetate (3×) the organic layers were combined, dried over magnesium sulfate, filtered and evaporated in vacuo. The crude mixture was chromatographed (silica gel, 100% methylene chloride→1%→2%→3%→4%→5%→50%→100% ethyl acetate in ethyl acetate in methylene chloride) to provide the fully protected coumarin 10 (2.77 g). MS (ESI) m/z=443 (M+H$^+$)

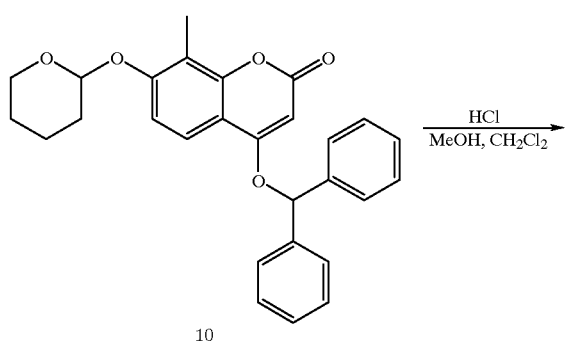

10

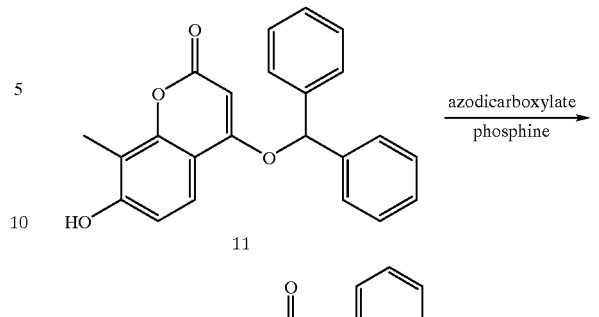

11

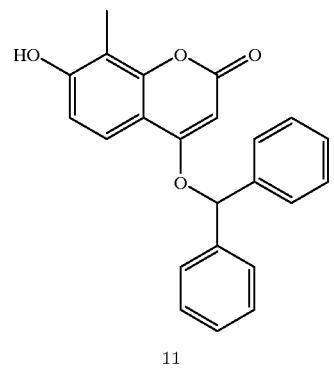

11

The procedure of Laurin, P. et al., *Bioorg. Med. Chem Lett.* 9, 2079 (1999) was followed. The coumarin 10 (2.77 g) was dissolved in anhydrous methylene chloride (20 mL) and anhydrous methanol (20 mL) and stirred at room temperature under nitrogen. Acetyl chloride (0.31 mL) was slowly dissolved in anhydrous methanol (5 mL) and added to the stirring solution of coumarin. After 90 minutes a white precipitate formed. The mixture was neutralized with aqueous saturated sodium bicarbonate and extracted with methylene chloride. The organic layer was dried over magnesium sulfate, filtered and evaporated. The coumarin 11 was purified by trituration with ethyl acetate. MS (ESI) m/z=359 (M+H$^+$).

SCHEME IV
Synthesis of PNC-Amine

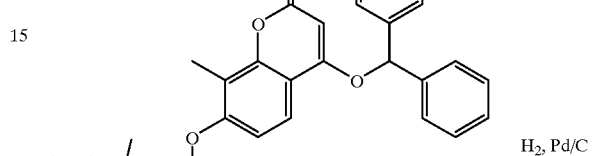

12

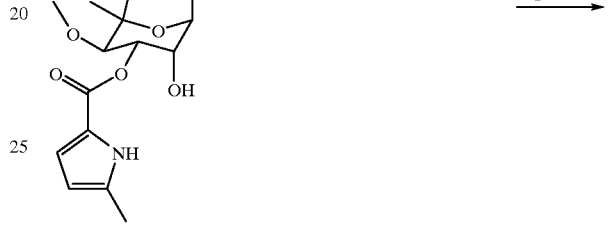

13

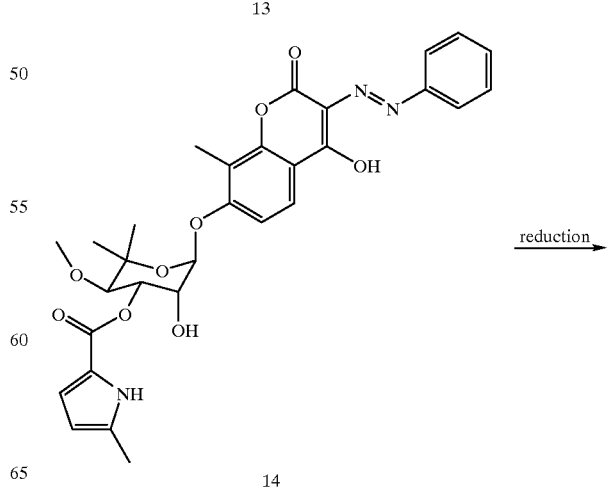

14

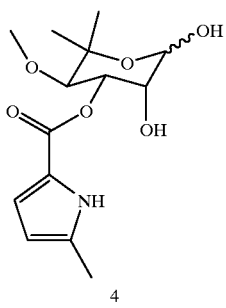

4

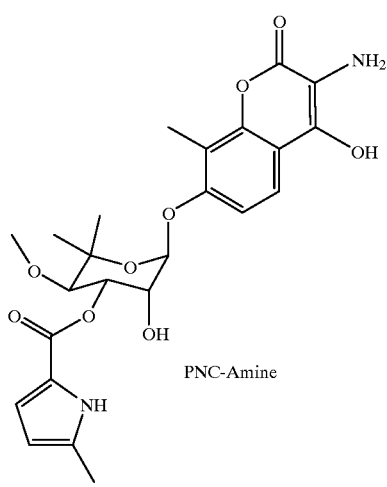

PNC-Amine

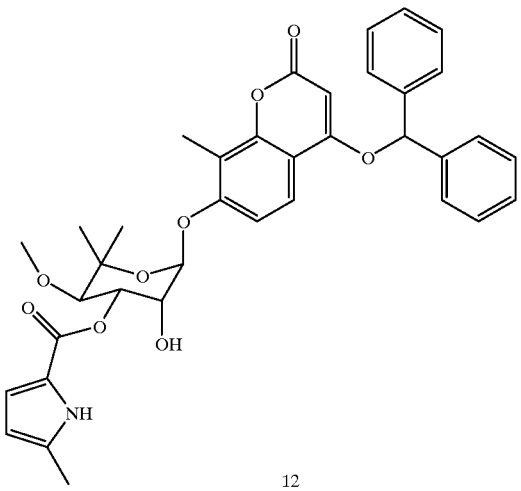

12

The pyrrole-sugar fragment 4 and the coumarin fragment 11 were coupled to form fragment 12. Preferably they were coupled using an azodicarboxylate and a phosphine derivative, more preferably they were coupled using diisopropylazodicarboxylate and triphenyl phosphine. The protecting group of 12 was removed by hydrogenolysis, preferably hydrogen gas in the presence of palladium, to provide 13. Diazotizaton of 13 with diazobenzene provided 14 that was reduced to the PNC-amine, (PNC=3-amino-4-hydroxy-8-methyl-7-[[3-O-[(5-methyl-2-pyrrolyl)carbonyl]noviosyl]oxy]coumarin) preferably with sodium dithionite.

The procedure of Laurin, P. et al., *Bioorg. Med. Chem Lett.* 9, 2079 (1999) was followed. The coumarin 11 (123 mg) and reducing sugar 4 (82.6 mg) were suspended in methylene chloride (5 mL) and stirred at room temperature under nitrogen. Triphenyl phosphine (101 mg) was added followed dropwise addition of diisopropyl azodicarboxylate (0.087 mL in 0.40 mL methylene chloride). After two hours, additional portions of triphenyl phosphine (36 mg) and diisopropyl azodicarboxylate (0.027) were added. Stirred under nitrogen overnight. Worked up by evaporation of methylene chloride in vacuo. Purified by repeated chormatography in silica gel (25%→33%→50% ethyl acetate in hexanes) to give the desired α-glycoside 12 (73 mg) and the undesired β-glycoside (32.6 mg). MS (ESI) m/z=640 (M+H⁺).

The PNC-amine is a late-stage building block that can be readily converted to the natural product coumermycin and many other dimeric coumarin derivatives, including those in the illustrated examples and in the claims section hereof.

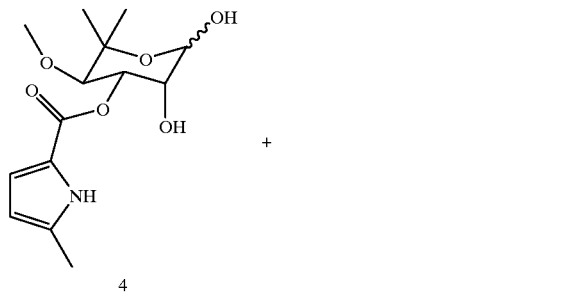

4

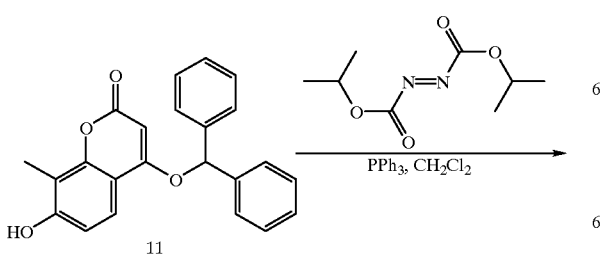

11

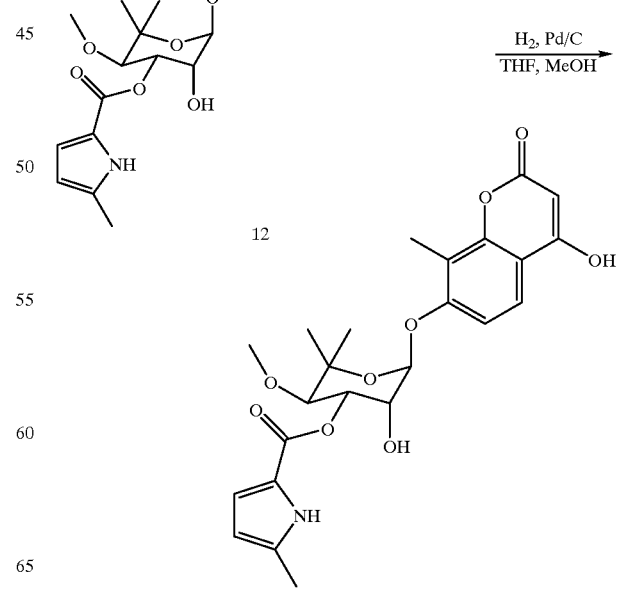

The α-glycoside 12 (73 mg) was dissolved in THF (2.5 mL) and ethanol (2.5 mL). Palladium on Carbon (10%, 14 mg) was added and the solution degassed. One atmosphere of hydrogen gas added and the reaction was stirred overnight. Hydrogen gas was removed in vacuo and the solution was filtered though celite. The eluant was evaporated and the solid 13 was taken crude to the next step. MS (ESI) m/z=474 (M+H$^+$).

a deep orange. The product was added to a saturated aqueous ammonium chloride solution and extracted with ethyl acetate (3×). The organic layers were combined, dried over magnesium sulfate and evaporated. The product 14 was taken to the next step without further purification. MS (ESI) m/z=578 (M+H$^+$).

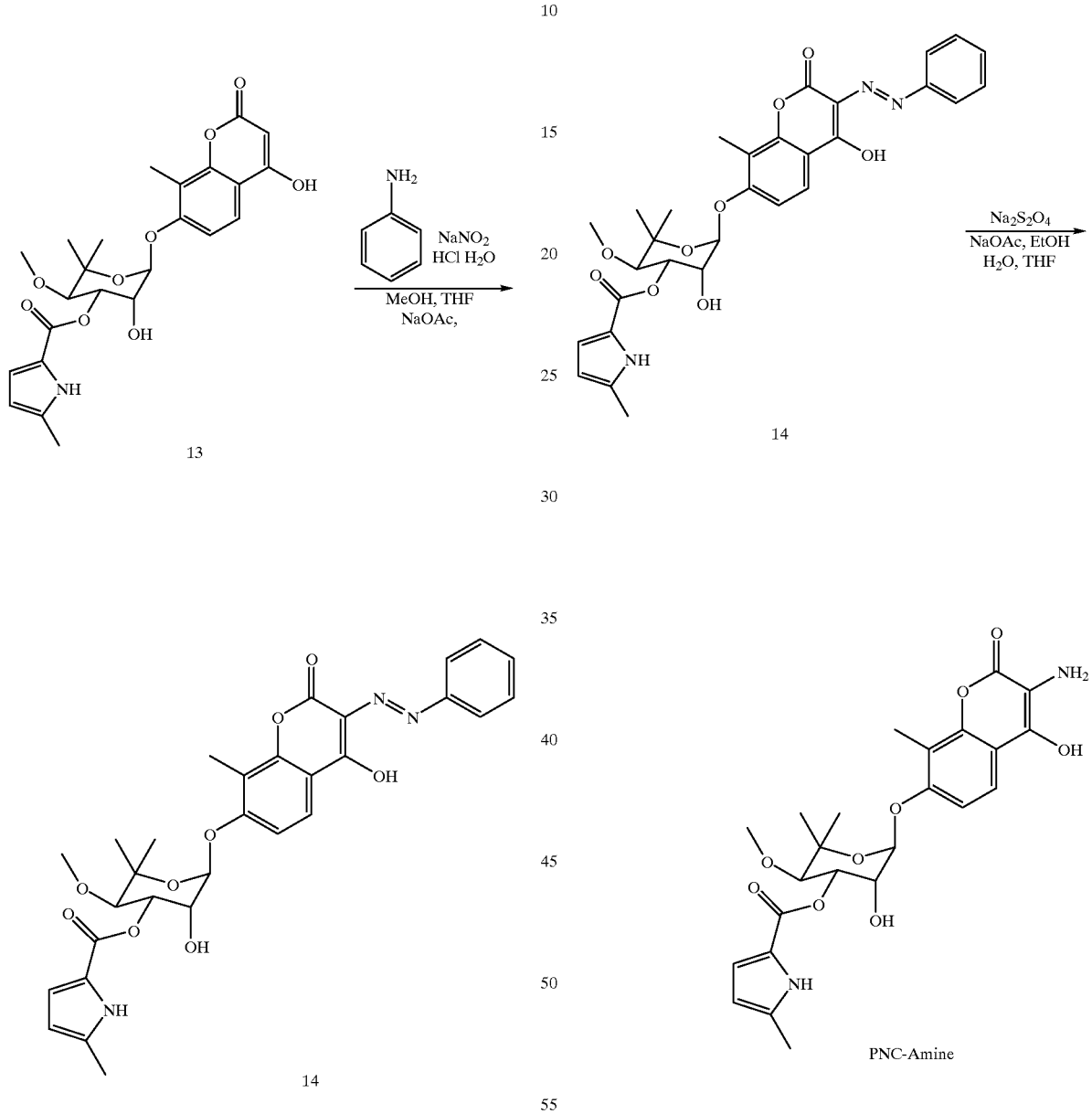

Aniline (0.10 mL) was added to a stirring solution of aqueous HCl (1N, 3.84 mL) at 0° C. Sodium nitrite was dissolved in water (0.35 mL) and added dropwise to the aniline solution. After 10 minutes, an aqueous solution of sodium acetate (405 mg in 0.70 mL water) was added and the resulting diazo benzene was stirred 10 additional minutes at 0° C. The noviose-coumarin 13 was dissolved in methanol (3 mL) and THF (1 mL) and stirred at room temperature. One equivalent of the diazobenzene solution was added dropwise to the coumarin and the solution turned The diazotized coumarin 14 was dissolved in THF (3 mL) and Ethanol (6 mL). The solution was stirred at room temperature and sodium acetate (56 mg dissolved in 1 mL water) was added. Sodium dithionate (80 mg) was then added and the solution turned from dark orange to light yellow. The solvents were then dried in vacuo and resulting crude PNC-amine was purified by silica gel chromoatography. (1:9:90 ammonium hydroxide:methanol:methylene chloride→2:18:80→3:27:70) to give pure PNC-amine (48.1 mg). MS (ESI) m/z=489 (M+H$^+$).

SCHEME V
Preparation of Coumermycin Analogs
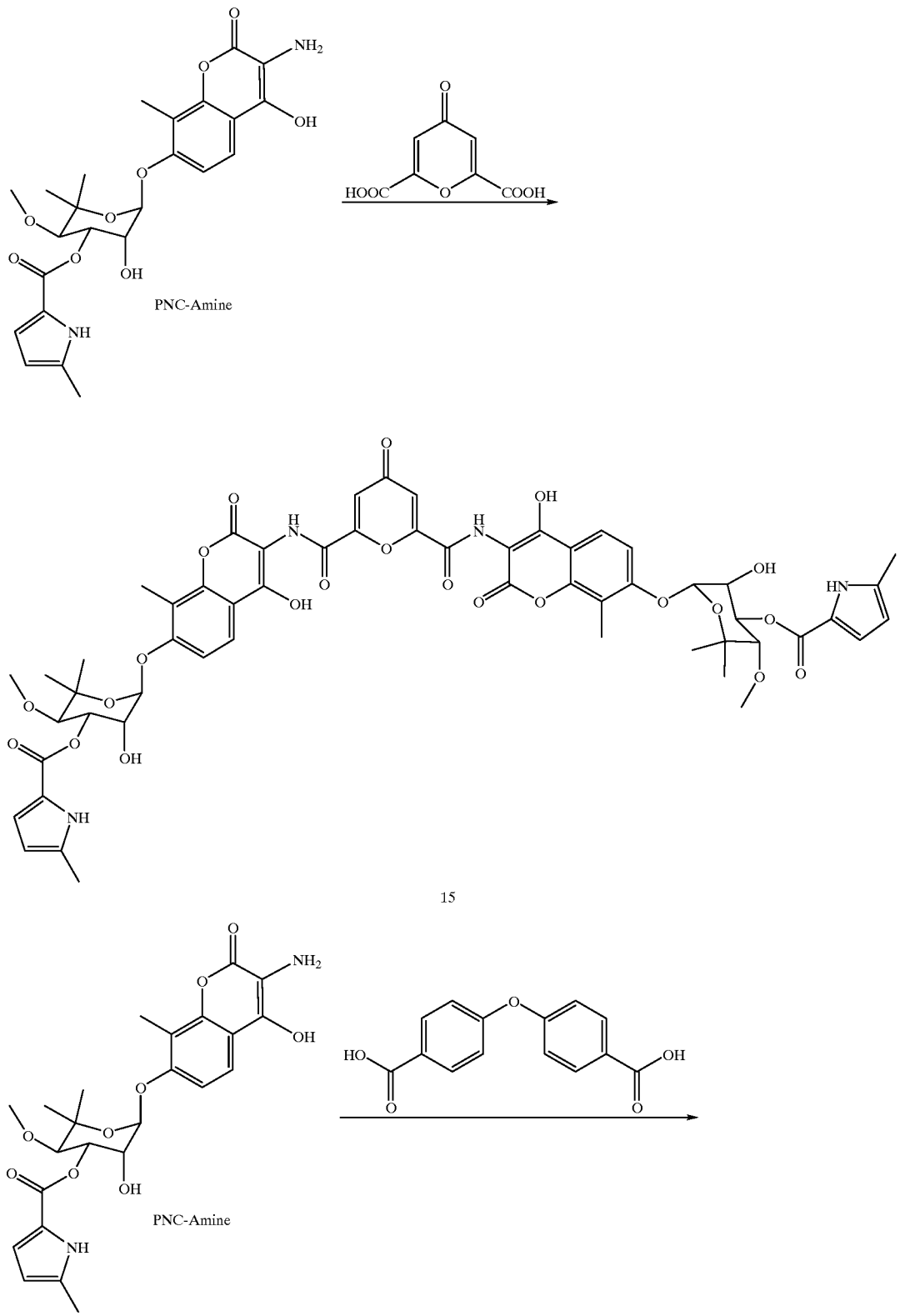

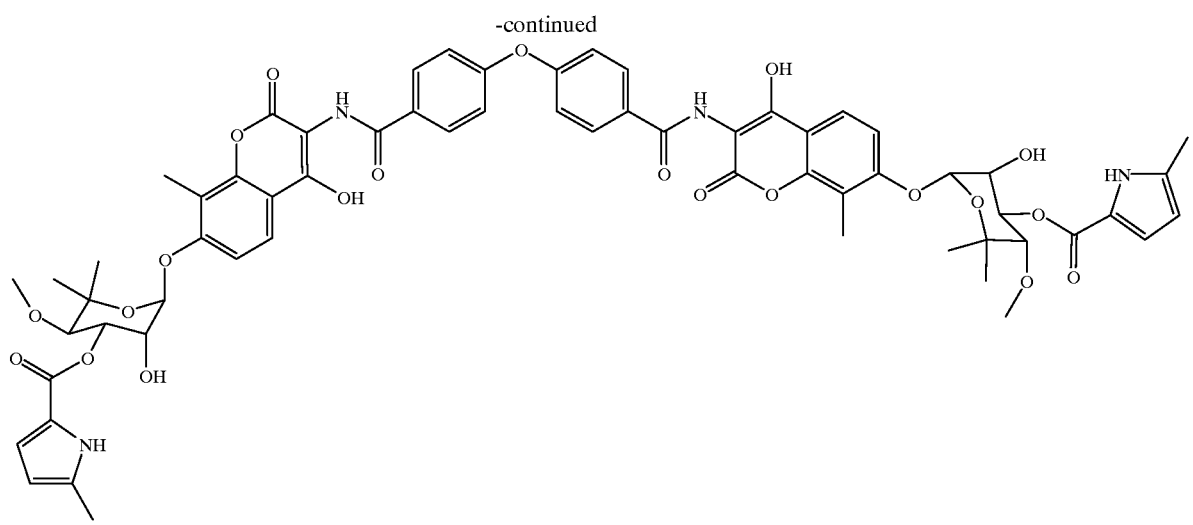

16

The coumarin analogs were prepared by the method shown in Scheme V. The PNC-Amine was exposed to a dicarboxylic acid or a derivative thereof to yield coumarin derivatives such as 15 and 16. Preferably, the PNC-Amine was exposed to a dicarboxylic acid and a peptide coupling reagent, most preferably the peptide coupling reagent was O-(azabenzotriazole-1-yl) N,N,N',N'-tetramethyluronium hexafluorophosphate).

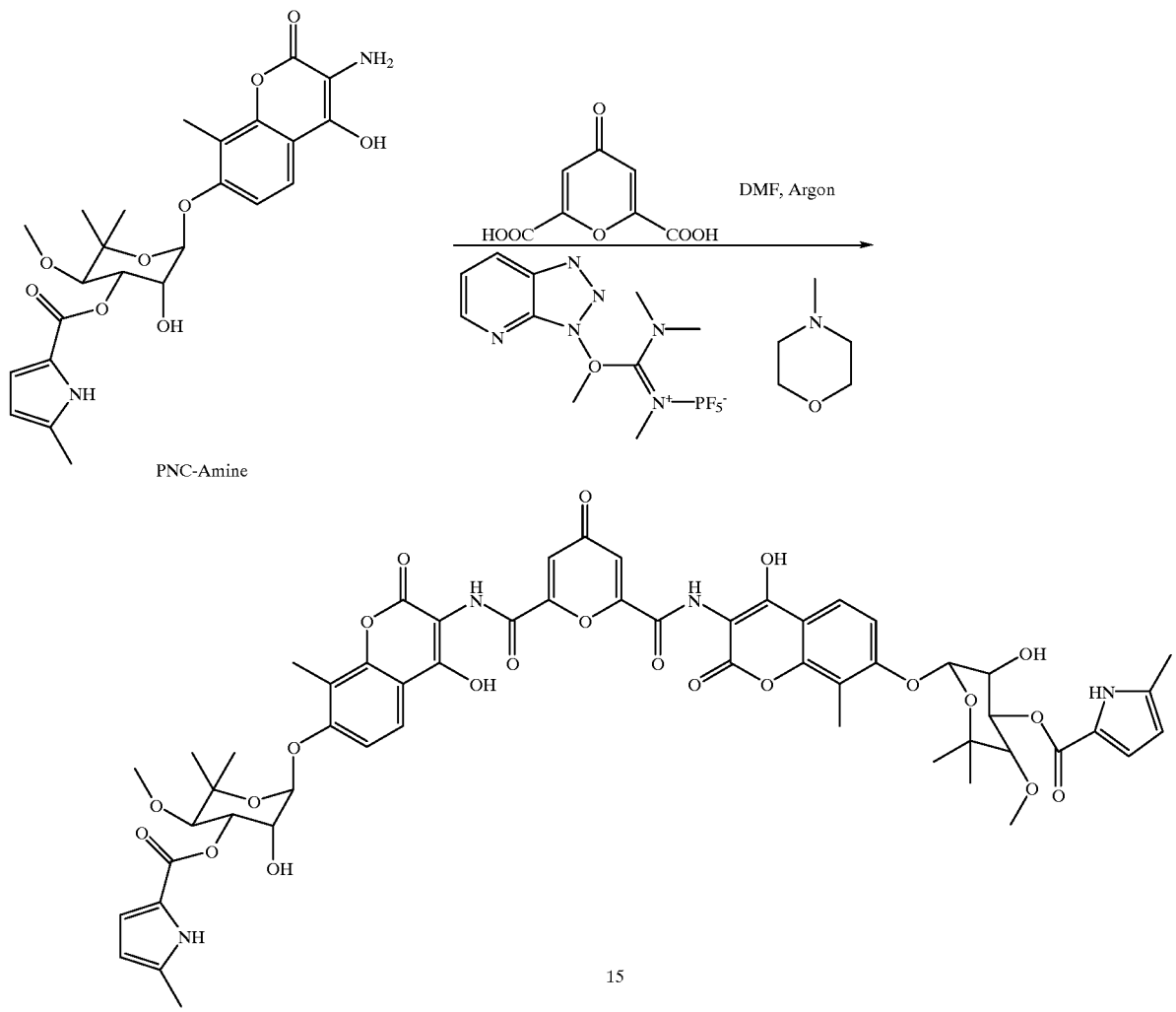

15

Chelidonic acid (2.9 mg) and O-(azabenzotriazole-1-yl) N,N,N',N'-tetramethyluronium hexafluorophosphate) (14.2 mg) were dissolved in dry deoxygenated DMF (1 mL) and stirred at room temperature under argon. 4-methylmorpholine (10.0 mL) was added to the reaction. After 15 minutes, PNC-amine (21.4 mg) was dissolved in dry deoxygenated DMF (0.4 mL) and added slowly to the activated diacid. The reaction was stirred overnight over argon and after 12 hours, the crude DMF solution was purified by injecting the solution onto the HPLC column where the final product 15 (3.3 mg) was readily purified (RP18, gradient, 90% $H_2O \rightarrow 100\%$ acetonitrile). MS (ESI) m/z=1125 (M+H$^+$).

Biological Evaluation

To evaluate the effectiveness of the analogs of the present invention to act as chemical dimerizers of chimeric proteins, a BAF cell proliferation assay was performed.

BAF Cell Proliferation Assay

BAF cells are known in the art and are a murine cell line that is dependent on cytokine stimulation for growth. We have transfected BAF Cells with the human IL2 Receptor β chain. These transfected cells respond to human IL-2 by increasing their rate of cellular proliferation. This can be assayed by measuring the amount of tritiated thymidine that these cells incorporate into their DNA. One of the signaling proteins activated by IL-2 is the transcription factor STAT5b. This activation of STAT5b is responsible, in part, for the growth-promoting effects of IL-2.

STAT5b is activated by dimerization, an event that is dependent on its phosphorylation and which requires interaction of STAT5b with a ligand bound activated receptor. We can mimic this activation of STAT5b by transfecting BAF cells with a fusion protein consisting of the GyrB domain (the 24 kDa amino-terminal fragment of bacterial DNA gyrase, amino acids 2–220) fused to the carboxy-terminus of STAT5b. Addition of the symmetrically dimeric antibiotic coumermycin artificially forces the dimerization of STAT5b-GyrB fusion proteins and results in an increased rate of cell growth that can be measured by the cell's ability to incorporate thymidine. This provides an assay to determine the

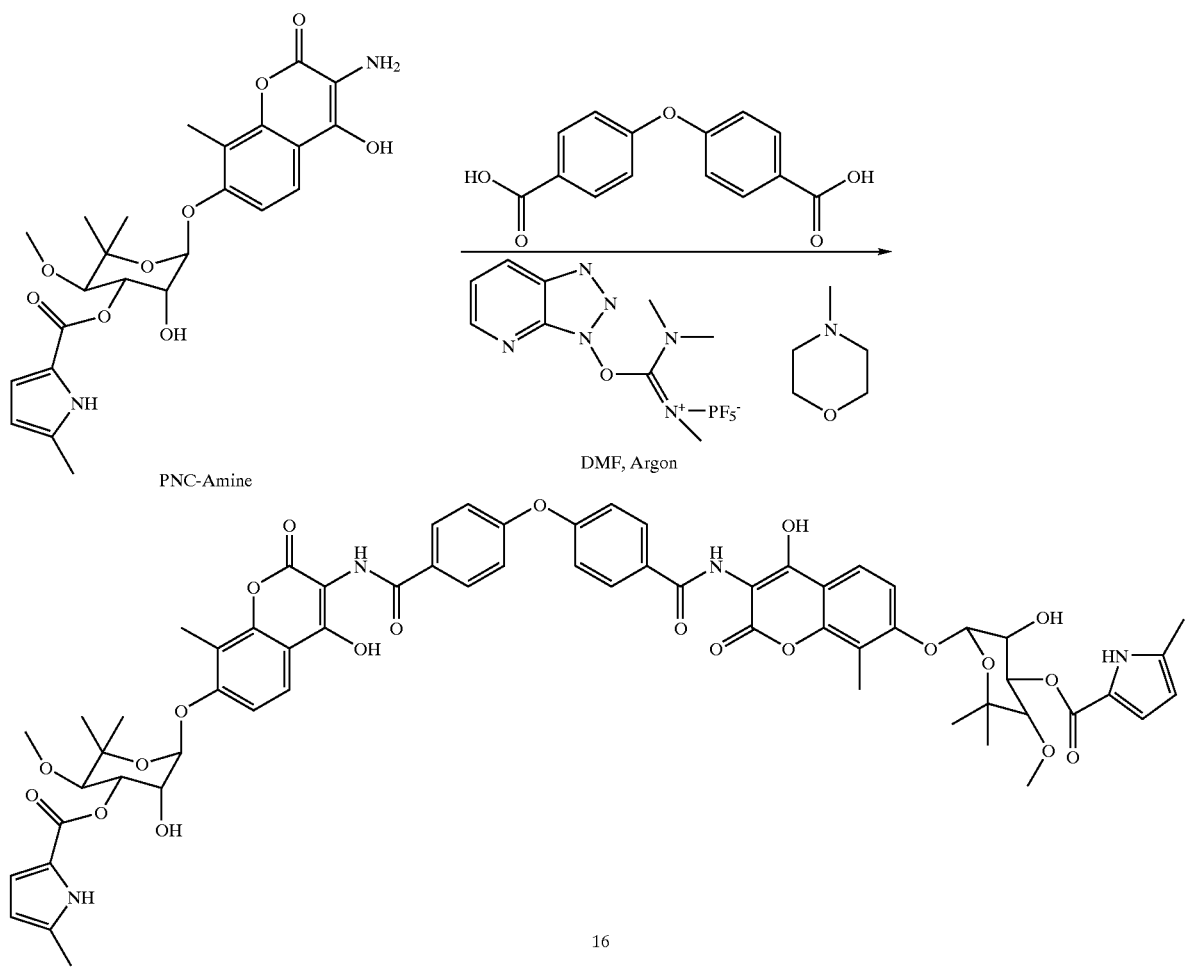

16

4,4;-oxybis(benzoic acid) (4.5 mg) and O-(azabenzotriazole-1-yl) N,N,N',N'-tetramethyluronium hexafluorophosphate) (13.2 mg) were dissolved in dry deoxygenated DMF (1 mL) and stirred at room temperature under argon. 4-methylmorpholine (10.5 μL) was added to the reaction. After 15 minutes, PNC-amine (23.6 mg) was dissolved in dry deoxygenated DMF (0.3 mL) and added slowly to the activated diacid. The reaction was stirred overnight over argon and after 12 hours, the crude DMF solution was purified by injecting the solution on to an HPLC column where the final product 16 was readily purified (RP18, gradient, 90% $H_2O \rightarrow 100\%$ acetonitrile). MS (ESI) m/z=1199 (M+H$^+$). Other coumermycin analogs were prepared using an identical method.

ability of coumermycin analogs to promote dimerization of STAT5b-GyrB fusion proteins.

The assay is run as follows: BAF cells transfected with the human IL-2 receptor β chain and STAT5b-GyrB are washed twice in phosphate-buffered saline. They are then re-suspended in BAF cell media that lacks IL-2 and placed in a 96-well plate. Increasing amounts of coumermycin, or coumermycin analogs are then added to different wells in a 96-well plate and the cells are incubated overnight. Twenty-four hours later the cell media is spiked with tritiated thymidine and the cells are incubated for an additional 16 hours. The cells are subsequently harvested with a Wallac cell harvester and the amount of tritiated thymidine incorporated is measured using a β scintillation counter.

EXAMPLES

The following examples are for the purpose of illustration of the invention, and in no way are meant to limit or deter the scope of the invention. Those skilled in the art, after reviewing the examples, will appreciate other, various methods in which the invention can be practiced.

The abbreviations used in the examples are as follows:
STAT=Signal Transducer and Activator of Transcription
IL=Interleukin as in Interleukin-2 (IL2)
PBS=Phosphate buffered saline
DMSO=Dimethyl Sulfoxide
BAF media
FCS=fetal calf serum
L-glu=the L form for glutamine
P/S=penicillin and streptomycin

Example 1

Compounds 5 and 6 were tested for BAF cell proliferation. Set up for BAF proliferation assay was as follows:

Spin down cells and wash one time in PBS. Resuspended in BAF cell media without cytokine at $2 \times 10^5$ cells/ml. added 100 μl/well or $2 \times 10^4$ cells. The compounds were prepared at 2 mg/ml (equivalent to 1.8 nM±5%). Plates were set up so that each condition equaled 1 row of 12 (n=number of wells/row=12). DMSO being utilized as an initial control Compound 5 was prepared in concentrations of 1.6, 16, 163, 450, and 900 nM, and 1.8 μM in DMSO, and as a second control, IL-2 growth factor was added to coumermycin. Two novenamine anologs, Comparative Compounds (CCmpd) 1 and 2, below were also use in this example as control. It is known that novenamine analogs penetrate BAF cells poorly. The comparative novenamine compounds are as follows:

Comparative Cmpd. 1

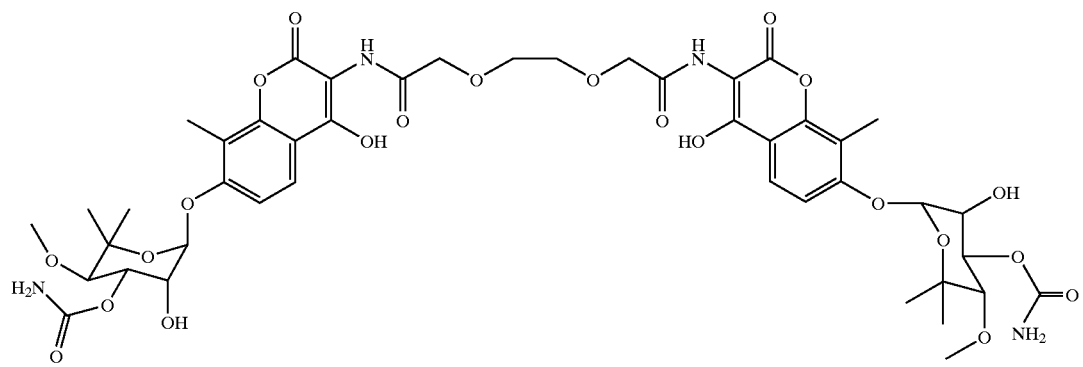

Comparative Cmpd. 2

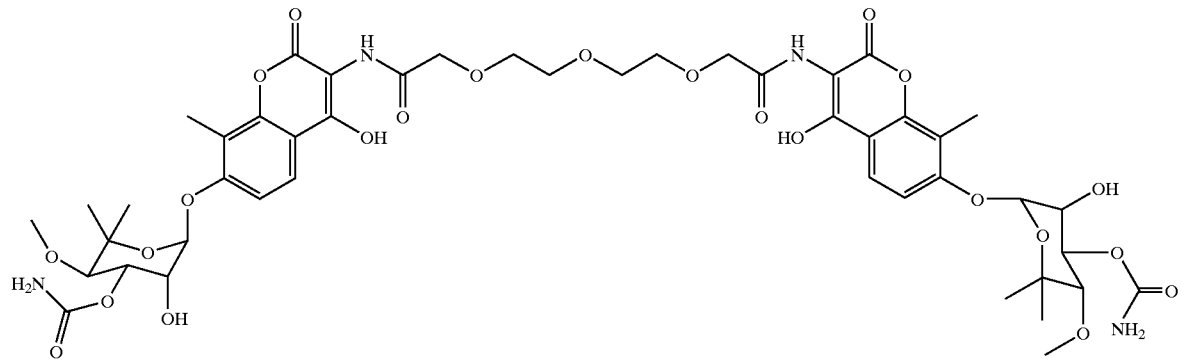

NEAA=Non-Essential Amino Acids
RPMI=cell growth media (Roswell Park Memorial Institute medium)

Table 2 provides the concentration for the coumermycin control and compounds, as well as the proliferation results and number of wells/row (n) of the microplate.

TABLE 2

Proliferation of STAT5b-GyrB Transfected BAF Cells Following Stimulation with Coumermycin or Coumermycin Analogs

| 1 Stimulus | 2 Conc. | 3 Prolif. | 4 S.D. | 5 n | 6 Stimulus | 7 Conc. | 8 Prolif. | 9 S.D. 2 | 10 N |
|---|---|---|---|---|---|---|---|---|---|
| DMSO | 0.1 | 15977 | 2549 | 12 | DMSO | 0.1 | 16215 | 1181 | 12 |
| Cou. 1.6 nM | 1.6 | 16137 | 1090 | 12 | Cmpd 5 1.6 nM | 1.6 | 15270 | 1157 | 12 |
| Cou. 16.3 nM | 16 | 16261 | 1342 | 12 | Cmpd 5 16.3 nM | 16 | 14277 | 1366 | 12 |
| Cou. 163 nM | 163 | 16836 | 3017 | 12 | Cmpd 5 163 nM | 163 | 14139 | 1182 | 12 |
| Cou. 450 nM | 450 | 18842 | 2046 | 12 | Cmpd 5 450 nM | 450 | 12732 | 1010 | 12 |
| Cou. 900 nM | 900 | 21057 | 1239 | 11 | Cmpd 5 900 nM | 900 | 12315 | 941 | 12 |
| Cou. 1.8 µM | 1800 | 23199 | 1402 | 11 | Cmpd 5 1.8 µM | 1800 | 11751 | 960 | 12 |
| IL-2 | | 103613 | 7231 | 12 | IL-2 | | 104407 | 10989 | 12 |
| DMSO | 0.1 | 15971 | 1335 | 10 | DMSO | 0.1 | 17296 | 950 | 12 |
| Cmpd 6 1.6 nM | 1.6 | 14954 | 828 | 12 | CCmpd 2 1.6 nM | 1.6 | 14761 | 819 | 11 |
| Cmpd 6 16.3 nM | 16 | 14710 | 963 | 12 | CCmpd 2 16.3 nM | 16 | 14459 | 2101 | 12 |
| Cmpd 6 163 nM | 163 | 13351 | 884 | 12 | CCmpd 2 163 nM | 163 | 14516 | 1239 | 12 |
| Cmpd 6 450 nM | 450 | 12190 | 929 | 11 | CCmpd 2 450 nM | 450 | 13568 | 1428 | 12 |
| Cmpd 6 900 nM | 900 | 12872 | 890 | 12 | CCmpd 2 900 nM | 900 | 12281 | 630 | 12 |
| Cmpd 6 1.8 µM | 1800 | 10832 | 572 | 12 | CCmpd 2 1.8 µM | 1800 | 11676 | 1025 | 12 |
| IL-2 | | 108500 | 7069 | 12 | IL-2 | | 109880 | 5033 | 12 |
| DMSO | 0.1 | 16755 | 1269 | 12 | | | | | |
| CCmpd 1 1.6 nM | 1.6 | 15741 | 1283 | 12 | | | | | |
| CCmpd 1 16.3 nM | 16 | 14691 | 1354 | 12 | | | | | |
| CCmpd 1 163 nM | 163 | 13628 | 1796 | 12 | | | | | |
| CCmpd 1 450 nM | 450 | 12465 | 1108 | 12 | | | | | |
| CCmpd 1 900 nM | 900 | 11935 | 901 | 12 | | | | | |
| CCmpd 1 1.8 µM | 1800 | 11057 | 901 | 12 | | | | | |
| IL-2 | | 104616 | 4807 | 12 | | | | | |

Example 2

In this example, Compounds 3, 4, 7, 8 and 9 were tested in BAF cell assays. The compounds were re-suspended in dimethylsulfoxide (DMSO) at a concentration of 2 mg/ml. Compounds 7 and 9 appeared slightly "purple" after dissolving in DMSO, perhaps a suggestion of some contamination with PNC-Amine. Next, the cells were washed 2 times with PBS. The re-suspended cells were present at a concentration of $1\times10^5$ cells /ml in BAF media (RPMI, 10% FCS (fetal calf serum), 1% NEAA (non-essential amino acid), 1% L-G-lu, P/S and Hepes) without IL-2, added 100 µl to well (equal to $1\times10^4$ cells/well).

The compounds were prepared in as follows: DMSO was used as a control; each of the 5 compounds were combined with DMSO at concentrations of 1.8 µM, 900 nM, 450 nM, 90 nM 9 nM, and 900 nM. As a second control, coumermycin in IL-2 was utilized. Each solution at the aforementioned concentration condition, along with BAF cells, was placed in 1 row (12 wells) of a 96 well plate. Thereafter, 100 µL of compound (twice the concentration) was added to the wells. After 24 hours, 3-H thymidine was added to the wells, and the assays were harvested.

Table 3 provides the DMSO concentration for the coumermycin control and compounds, as well as the proliferation results and number of wells/row (n) of the microplate.

TABLE 3

Proliferation of STAT5b-GyrB Transfected BAF Cells Following Stimulation with Coumermycin or Coumermycin Analogs

| 1 Compound | 2 Conc. (graph) | 3 Prolif. (cpm | 4 S.D. | 5 N | 6 Compound | 7 Prolif. (cpm) | 8 S.D. 2 | 9 N |
|---|---|---|---|---|---|---|---|---|
| DMSO | 0.09 | 20912 | 1514 | 72 | DMSO | 20912 | 1514 | 72 |
| Cou. 900 pM | 0.9 | 18071 | 1690 | 12 | Cmpd 8 90 | 17973 | 1657 | |

TABLE 3-continued

Proliferation of STAT5b-GyrB Transfected BAF Cells Following Stimulation with Coumermycin or Coumermycin Analogs

| 1 Compound | 2 Conc. (graph) | 3 Prolif. (cpm | 4 S.D. | 5 N | 6 Compound | 7 Prolif. (cpm) | 8 S.D. 2 | 9 N |
|---|---|---|---|---|---|---|---|---|
| Cou. 9 nM | 9 | 20551 | 1903 | 12 | Cmpd 8 9 pM | 19377 | 1209 | |
| Cou. 90 nM | 90 | 25219 | 1159 | 12 | Cmpd 8 9 nM | 20715 | 1860 | |
| Cou. 450 nM | 450 | 27515 | 1907 | 12 | Cmpd 8 900 nM | 22936 | 1241 | |
| Cou. 900 nM | 900 | 30752 | 1743 | 12 | Cmpd 8 450 nM | 23858 | 1276 | |
| Cou. 1.8 µM | 1800 | 30664 | 1950 | 12 | Cmpd 8 900 nM | 22772 | 1806 | |
| IL-2 | | 98745 | 7073 | 72 | Cmpd 8 1.8 µM | | | |
| DMSO | 0.09 | 20912 | 1514 | 72 | IL-2 | 98745 | 7073 | 72 |
| Cmpd 9 900 nM | 0.9 | 16826 | 1703 | | DMSO | 20912 | 1514 | 72 |
| Cmpd 9 9 nM | 9 | 18126 | 984 | | Cmpd 7 900 pM | 16520 | 1628 | |
| Cmpd 9 90 nM | 90 | 19177 | 1495 | | Cmpd 7 9 nM | 16599 | 1617 | |
| Cmpd 9 450 nM | 450 | 20889 | 1588 | | Cmpd 7 90 nM | 17690 | 1562 | |
| Cmpd 9 900 µM | 900 | 22210 | 2013 | | Cmpd 7 450 nM | 20553 | 1402 | |
| Cmpd 9 1.8 µM | 1800 | 20367 | 1428 | | Cmpd 7 900 nM | 20619 | 1563 | |
| IL-2 | | 98745 | 7073 | 72 | Cmpd 7 1.8 µM | 20207 | 1598 | |
| DMSO | 0.09 | 20912 | 1514 | 72 | IL-2 | 98745 | 7073 | 72 |
| Cmpd 3 900 pM | 0.9 | 16313 | 1836 | | DMSO | 20912 | 1514 | 72 |
| Cmpd 3 9 nM | 9 | 16767 | 1622 | | Cmpd 4 900 pM | 20204 | 1825 | |
| Cmpd 3 90 nM | 90 | 19920 | 1482 | | Cmpd 4 9 nM | 19290 | 2532 | |
| Cmpd 3 90 nM | 450 | 22221 | 1967 | | Cmpd 4 90 nM | 19731 | 1856 | |
| Cmpd 3 900 nM | 900 | 22824 | 2140 | | Cmpd 4 450 nM | 20726 | 1756 | |
| L880,078 1.8 µM | 1800 | 21389 | 1761 | | Cmpd 4 900 nM | 22817 | 2099 | |
| IL-2 | | 98745 | 7073 | 72 | Cmpd 4 1.8 µM | 23135 | 1410 | |
| | | | | | IL-2 | 98745 | 7073 | 72 |

Example 3

A proliferation assay of Compound 1 using BAF cells transfected with the human growth factor IL-2RB chain and STAT5b-GyrB.

The assay was set up using DMSO; Compound 1 in DMSO concentrations of 900 pM, 9 nM, 90 nM, 450 nM, 900 nM, and 1.8 µM; and IL-2, as a control. Compound 1, in rows of 12, containing the aforementioned concentrations of DMSO, coumermycin controls, and the cells were placed in wells of a microplate. After 24 hours 3H-thymidine at various concentrations was added to each well and allowed to proliferate.

Table 4 provides the DMSO concentration for the coumermycin control and compounds, as well as the proliferation results and number of wells/row (n) of the microplate.

TABLE 4

Proliferation of STAT5b-GyrB Transfected BAF Cells Following Stimulation with Coumermycin or Coumermycin Analogs

| Conc. | Conc. (graph) | Cou. Prolif. | S.D. | n | Cmpd 1 Prolif | S.D. 2 | N |
|---|---|---|---|---|---|---|---|
| DMSO | 0 | 8085 | 485 | 24 | 8085 | 485 | 24 |
| 900 pM | 0.9 | 7422 | 299 | 12 | 7156 | 773 | 12 |
| 9 nM | 9 | 8792 | 469 | 12 | 7653 | 409 | 12 |
| 90 nM | 90 | 9860 | 319 | 12 | 7487 | 440 | 12 |
| 450 nM | 450 | 10832 | 422 | 12 | 7209 | 292 | 12 |
| 900 nM | 900 | 11470 | 750 | 12 | 7092 | 344 | 11 |
| 1.8 µM | 1800 | 12308 | 618 | 12 | 6397 | 313 | 12 |
| IL-2 | | 31644 | 2005 | 24 | 31644 | 2005 | 24 |

Example 4

A proliferation assay of Compound 2 using BAF cells transfected with the human growth factor IL-2Rβ chain and STAT5b-GyrB.

The cells were placed in the wells at a concentration of $1 \times 10^4$ cells/well (in 100 µL=$1 \times 10^5$ cells/mL. The assay was set up using DMSO; Compound 2 in DMSO concentrations of 900 pM, 9 nM, 90 nM, 450 nM, 900 nM, and 1.8 µM; and IL-2, as a control. Compound 2, in rows of 12, containing the aforementioned concentrations of DMSO, coumermycin controls, and the BAF cells were placed in wells of a microplate. After 24 hours 3H-thymidine was added to each well and the cells were allowed to proliferate an additional 16 hours. FIG. 12 provides a graphical illustration of the results of the proliferation.

An inhibition assay was also conducted for Compounds 1 and 2. For this assay, all wells contained a DMSO concentration of 90 nM of coumermycin. Compounds 1 and 2 were added at concentrations of 1.8 μM, 900 nM, 90 nM and 9 nM. The conditions of the assay were identical to those referenced early in this example, except that one-third of the amount of 3-H thymidine was used.

Tables 5 and 6 provide the concentration for the coumermycin control and compounds, as well as the proliferation results and number of wells/row (n) of the microplate.

TABLE 5

Proliferation of STAT5b-GyrB Transfected BAF Cells Following Stimulation with Coumermycin or Coumermycin Analogs

| 1 Compound | 2 Conc. (graph) | 3 Prolif. (cpm) | 4 S.D. | 5 n | 6 Compound | 7 Prolif. (cpm) | 8 S.D. 2 | 9 N |
|---|---|---|---|---|---|---|---|---|
| DMSO | 0.09 | 6161 | 424 | 21 | DMSO | 6161 | 424 | 21 |
| Cou. 900 pM | 0.9 | 6063 | 367 | 11 | Cmpd 2 900 pM | 6014 | 344 | 10 |
| Cou. 9 nM | 9 | 6750 | 674 | 11 | Cmpd 2 9 nM | 6031 | 326 | 12 |
| Cou. 90 nM | 90 | 7595 | 437 | 10 | Cmpd 2 90 nM | 6623 | 241 | 11 |
| Cou. 450 nM | 450 | 8457 | 530 | 11 | Cmpd 2 450 nM | 7513 | 450 | 12 |
| Cou. 900 nM | 900 | 8636 | 607 | 11 | Cmpd 2 900 nM | 7798 | 463 | 11 |
| Cou. 1.8 uM | 1800 | 8610 | 553 | 11 | Cmpd 2 1.8 μM | 7825 | 343 | 12 |
| IL-2 | | 18285 | 681 | 12 | IL-2 | 18285 | 681 | 12 |

TABLE 6

| 1 Compound | 2 Inhibitor | 3 Conc. (graph) | 4 Prolif. | 5 S.D. | 6 n |
|---|---|---|---|---|---|
| Cou. 90 nM | DMSO | 0.9 | 7595 | 437 | 10 |
| Cou. 90 nM | Cmpd 1 9 nM | 9 | 7713 | 328 | 12 |
| Cou. 90 nM | Cmpd 1 90 nM | 90 | 7683 | 297 | 11 |
| Cou. 90 nM | Cmpd 1 900 nM | 900 | 7597 | 209 | 11 |
| Cou. 90 nM | Cmpd 1 1800 nM | 1800 | 7271 | 273 | 10 |
| Cou. 90 nM | DMSO | 0.9 | 7595 | 437 | 10 |
| Cou. 90 nM | Cmpd 2 | 9 | 7654 | 182 | 12 |
| Cou. 90 nM | Cmpd 2 | 90 | 7316 | 391 | 11 |
| Cou. 90 nM | Cmpd 2 | 900 | 8068 | 434 | 11 |
| Cou. 90 nM | Cmpd 2 | 1800 | 8165 | 467 | 11 |

Example 5

In this example, Compounds 1 and 2 were compared to 2 comparative novenamime compounds Comparative Compounds 3 and 4, for cell proliferation. The novenamime compounds are as follows:

Comparative Cmpd. 3

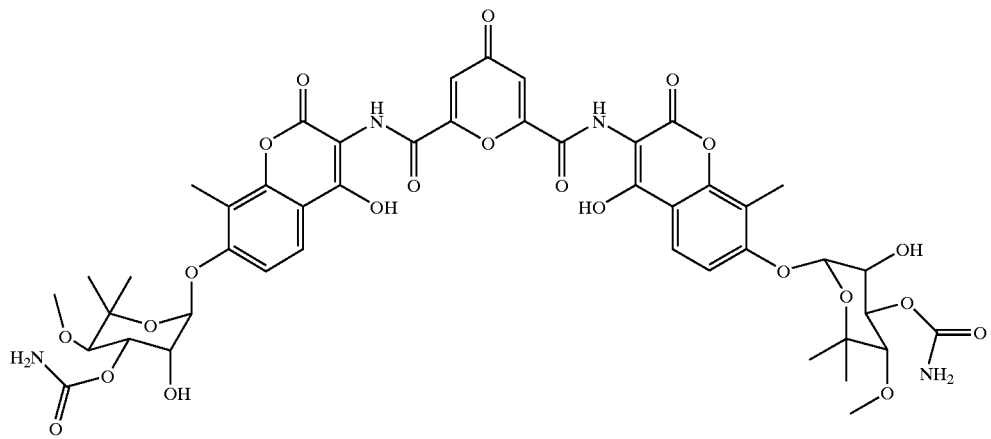

Comparative Cmpd. 4

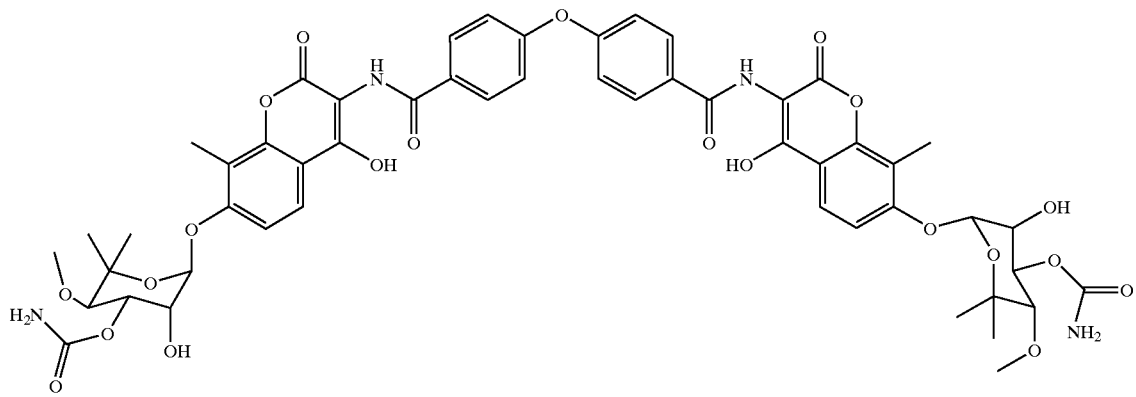

The procedure for preparing the compounds, coumermycin controls, as well as the addition of BAF cells and 3-H thymidine were performed in accordance with the Example 4, above.

Table 7 provides the concentration for the coumermycin control and compounds, as well as the proliferation results and number of wells/row (n) of the microplate.

TABLE 7

Proliferation of STAT5b-GyrB Transfected BAF Cells Following Stimulation with Coumermycin or Coumermycin Analogs

| 1<br>Compound | 2<br>Conc.<br>(graph) | 3<br>Prolif.<br>(cpm) | 4<br>S.D. | 5<br>n | 6<br>Compound | 7<br>Prolif.<br>(cpm) | 8<br>S.D. 2 | 9<br>N |
|---|---|---|---|---|---|---|---|---|
| DMSO | 0.09 | 33562 | 2947 | 55 | DMSO | 33562 | 2947 | 55 |
| Cou. 900 pM | 0.9 | 36503 | 3292 | 12 | Cmpd 2 900 pM | 36052 | 2457 | 11 |
| Cou. 9 nM | 9 | 44455 | 4059 | 11 | Cmpd 2 9 nM | 38236 | 3693 | 12 |
| Cou. 90 nM | 90 | 51248 | 5116 | 12 | Cmpd 2 90 nM | 42674 | 3503 | 12 |
| Cou. 450 nM | 450 | 60293 | 5465 | 12 | Cmpd 2 450 nM | 47023 | 4085 | 12 |
| Cou. 900 nM | 900 | 64831 | 6507 | 12 | Cmpd 2 900 nM | 46989 | 3129 | 12 |
| Cou 1.8 μM | 1800 | 68728 | 3753 | 12 | Cmpd 2 1.8 μM | 46345 | 3344 | 12 |
| IL-2 | | 131314 | 9382 | 60 | IL-2 | 131314 | 9382 | 60 |
| DMSO | 0.09 | 33562 | 2947 | 55 | DMSO | 33562 | 2947 | 55 |
| CCmpd 4 900 pM | 0.9 | 35624 | 3252 | 12 | Cmpd 1 900 pM | 31865 | 2146 | 12 |
| CCmpd 4 9 nM | 9 | 35985 | 4308 | 12 | Cmpd 1 9 nM | 34279 | 2795 | 12 |

TABLE 7-continued

Proliferation of STAT5b-GyrB Transfected BAF Cells Following Stimulation with Coumermycin or Coumermycin Analogs

| 1 Compound | 2 Conc. (graph) | 3 Prolif. (cpm) | 4 S.D. | 5 n | 6 Compound | 7 Prolif. (cpm) | 8 S.D. 2 | 9 N |
|---|---|---|---|---|---|---|---|---|
| CCmpd 4 90 nM | 90 | 36764 | 2451 | 11 | Cmpd 1 90 nM | 33933 | 2752 | 12 |
| CCmpd 4 450 nM | 450 | 36763 | 3258 | 12 | Cmpd 1 450 nM | 35212 | 2613 | 12 |
| CCmpd 4 900 nM | 900 | 35379 | 3452 | 11 | Cmpd 1 900 nM | 33301 | 2530 | 12 |
| CCmpd 4 1.8 µM | 1800 | 31918 | 2788 | 11 | Cmpd 1 1.8 µM | 31029 | 2035 | 12 |
| IL-2 | | | | | IL-2 | 131314 | 9382 | 60 |
| DMSO | 0.09 | 33562 | 2947 | 55 | | | | |
| CCmpd 3 900 pM | 0.9 | 32299 | 3045 | 12 | | | | |
| CCmpd 3 9 nM | 9 | 33921 | 2985 | 12 | | | | |
| CCmpd 3 90 nM | 90 | 33671 | 4001 | 11 | | | | |
| CCmpd 3 450 nM | 450 | 33712 | 2205 | 12 | | | | |
| CCmpd 3 900 nM | 900 | 31968 | 3032 | 12 | | | | |
| CCmpd 3 1.8 µM | 1800 | 28434 | 1564 | 11 | | | | |
| IL-2 | | 131314 | 9382 | 60 | | | | |

What is claimed is:

1. A compound of the formula I:

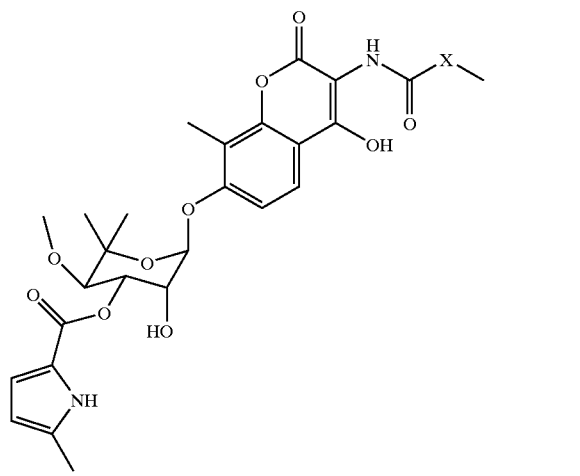

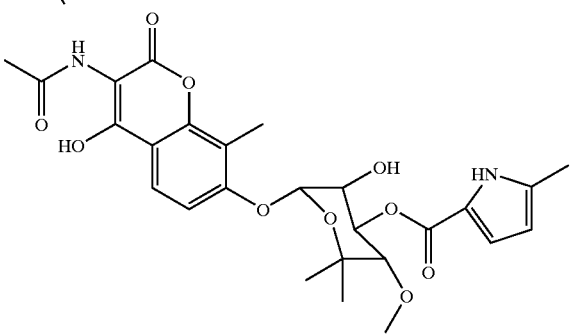

or a pharmaceutically acceptable salt or ester thereof, wherein X is a linking group selected from the group consisting of straight, branched and cyclic alkyl, aryl, diaryl, heteroaryl, said alkyl, aryl, diaryl and heteroaryl optionally substituted with 1–3 groups of $C_{1-6}$ alkyl or $NH_2$, alkyl with 1–3 heteroatoms in the chain, and a combination of alkyl, aryl and/or heteroaryl substituents, provided that when X is a substituted heteroaryl it is not

2. The compound according to claim 1 wherein X is selected from the group consisting of pyrrole, pyridine, furan, indole, benzofuran, dibenzofuran, thiophene, straight chain alkyl, cycloalkyl, phenyl, diaryl and combinations thereof.

3. The compound according to claim 2, wherein pyrrolyl is selected from the group consisting of

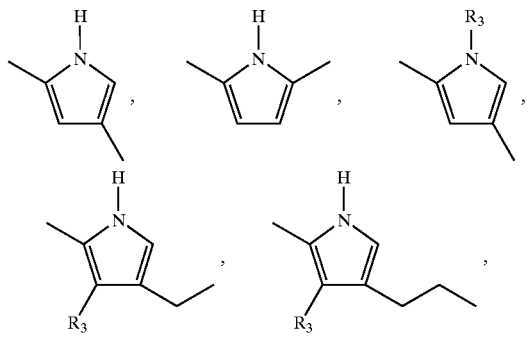

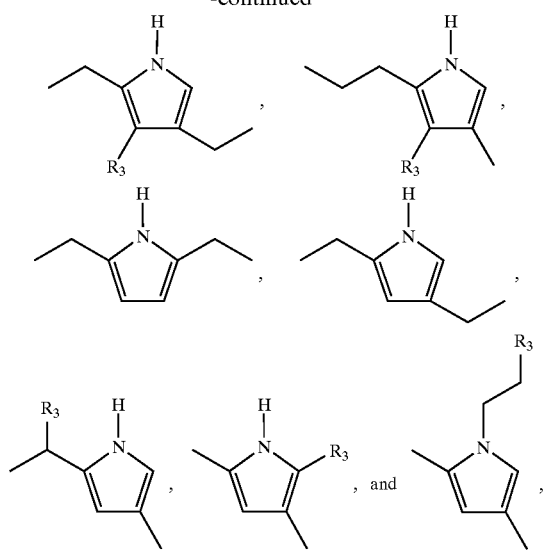

wherein R₃ is H or CH₃.

4. The compound according to claim 2, wherein diaryl is selected from the group consisting of

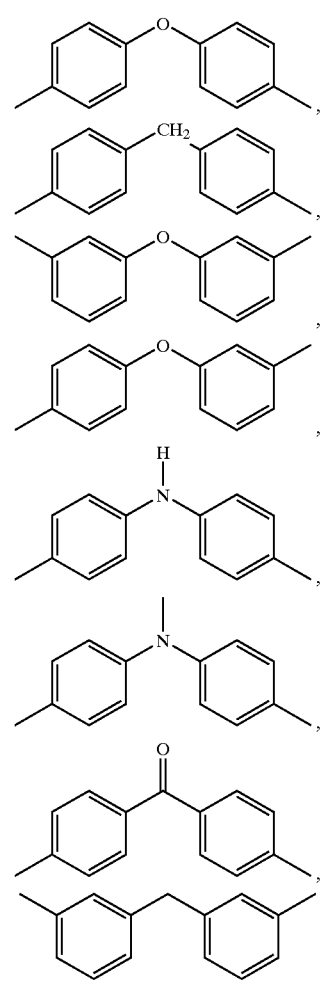

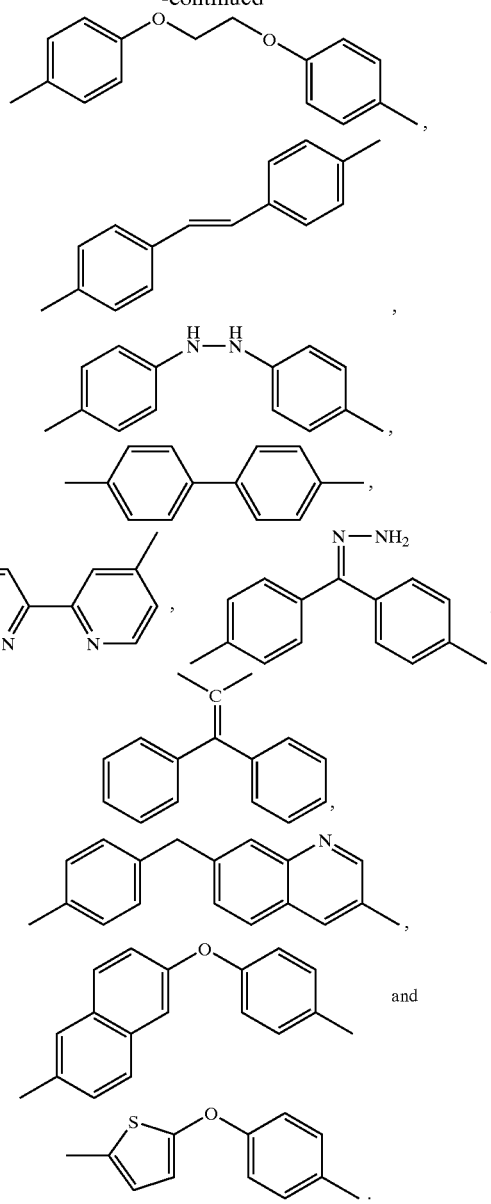

5. The compound according to claim 2, wherein pyridinyl is selected from the group consisting of

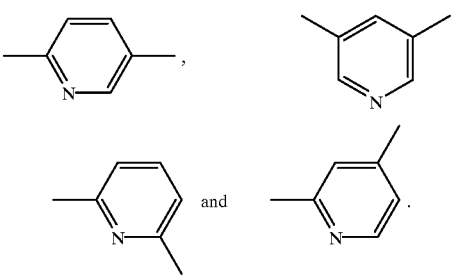

6. The compound according to claim 2, wherein X is a straight chain alkyl which contains between one and eighteen carbons.

7. The compound according to claim 2, wherein indolyl is selected from the group consisting of

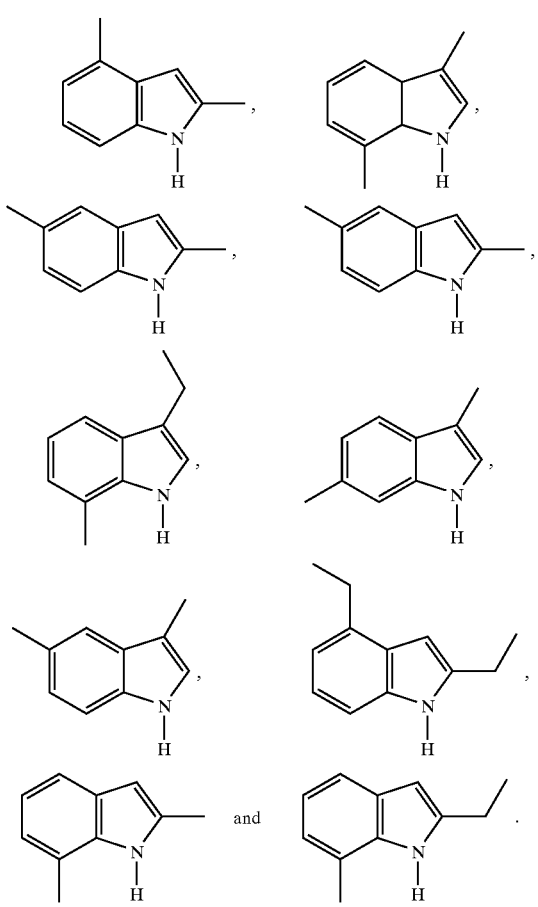

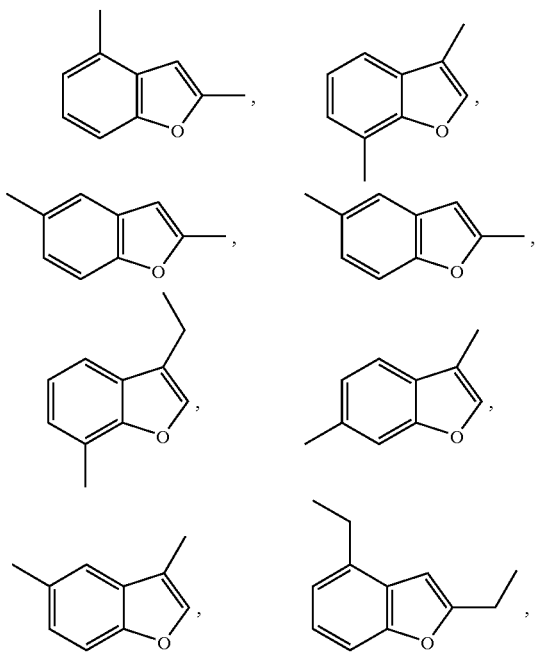

8. The compound according to claim 2, wherein benzofuranyl is selected from the group consisting of

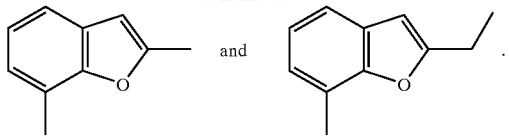

9. The compound according to claim 2, wherein phenyl is selected from the group consisting of

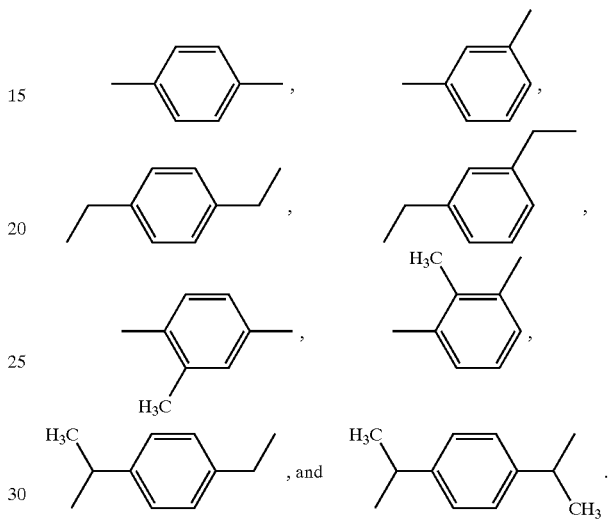

10. The compound according to claim 2, wherein cycloalkyl is selected from the group consisting of

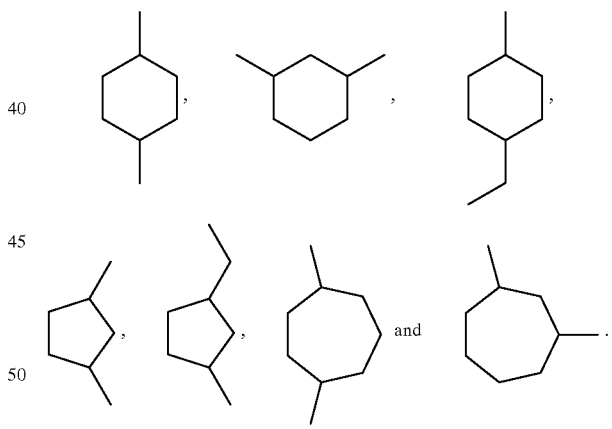

11. The compound according to claim 2, wherein furanyl is selected from the group consisting of

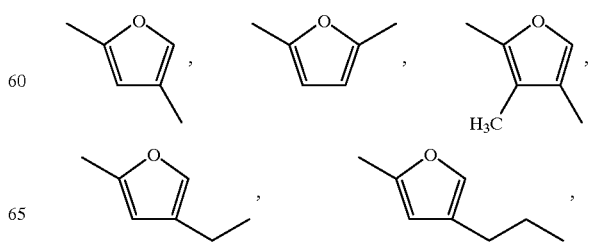

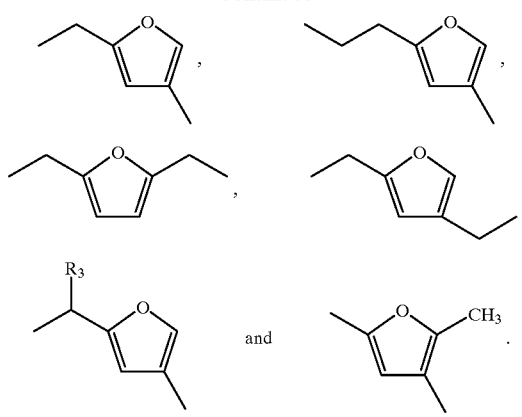
12. The compound according to claim 2, wherein dibenzofuranyl is selected from the group consisting of
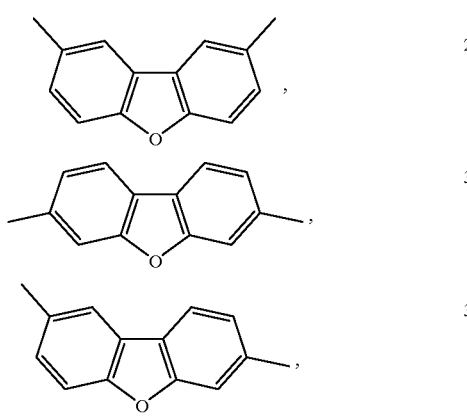
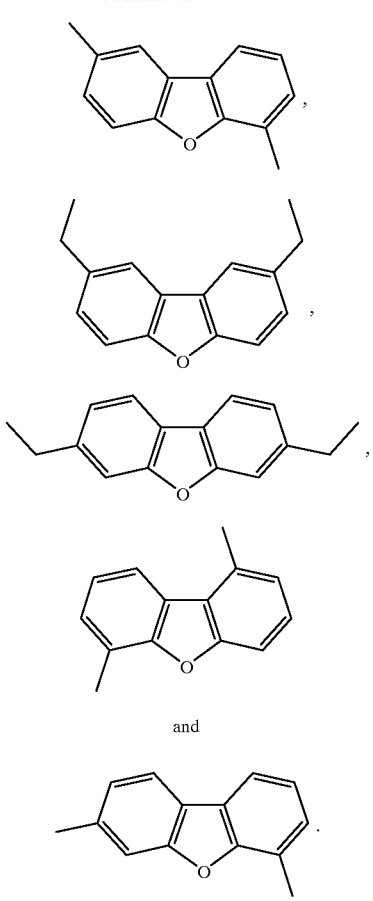
13. A compound selected from the group consisting of
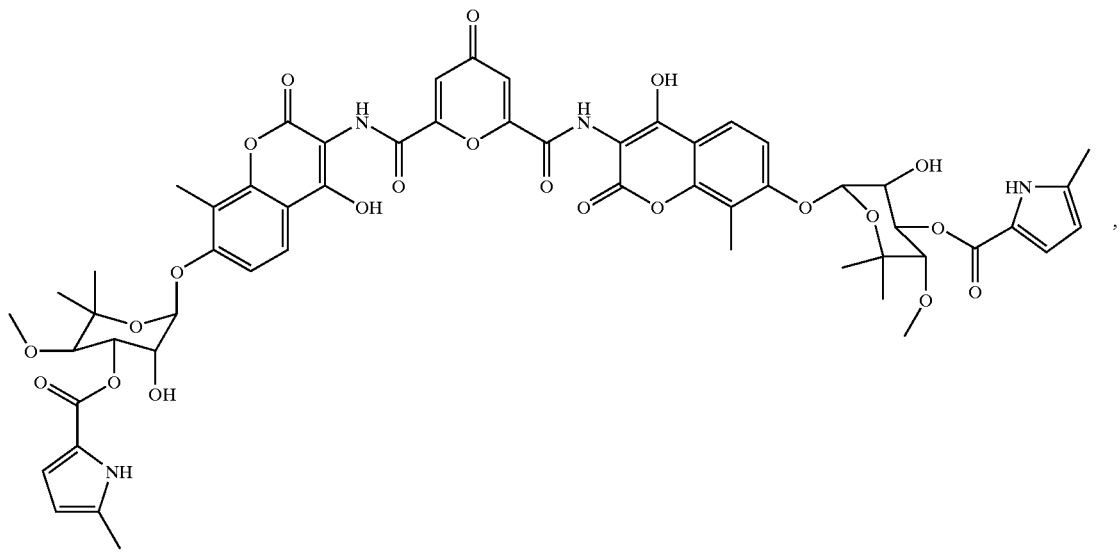

-continued
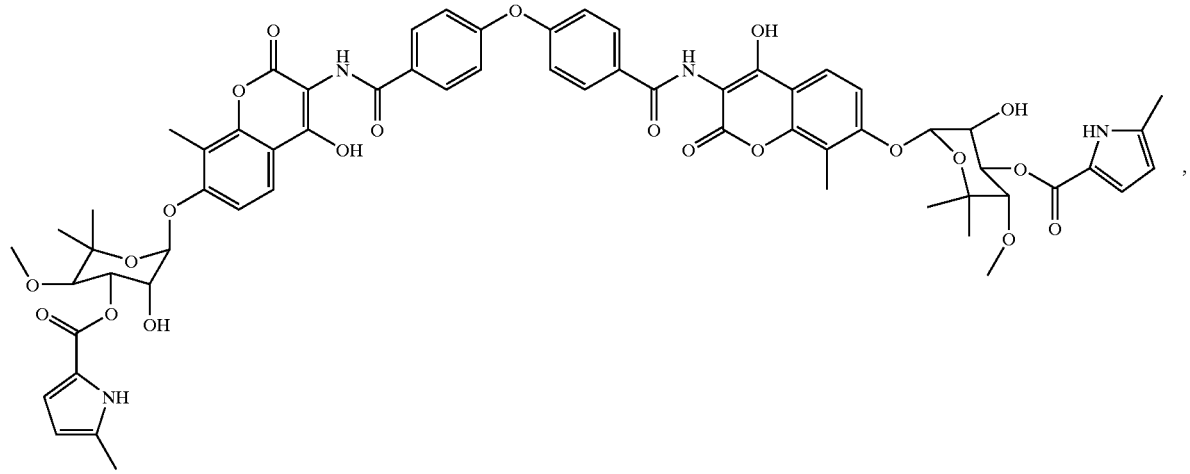
,
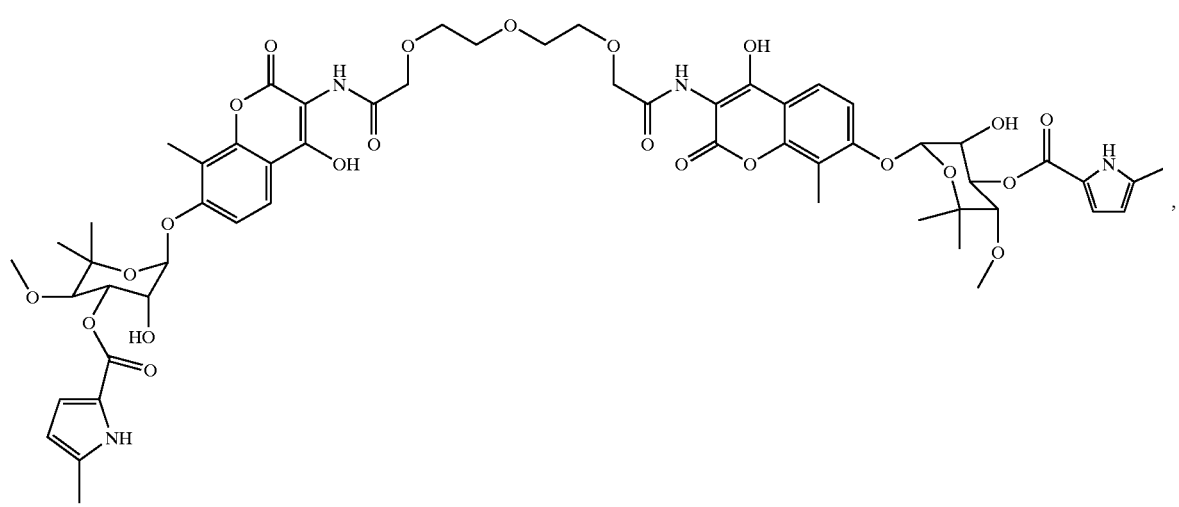
,
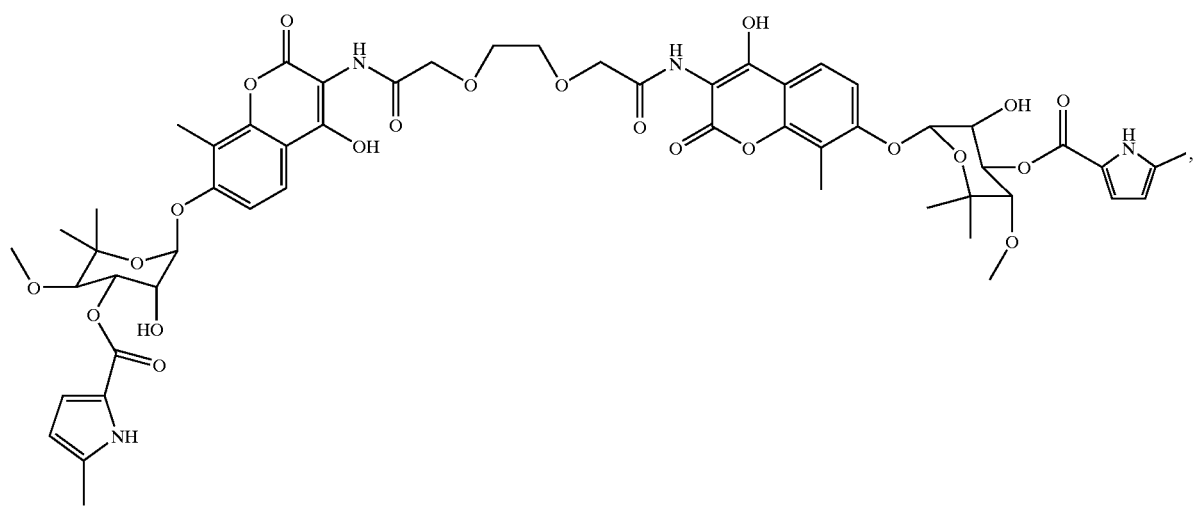
;

-continued
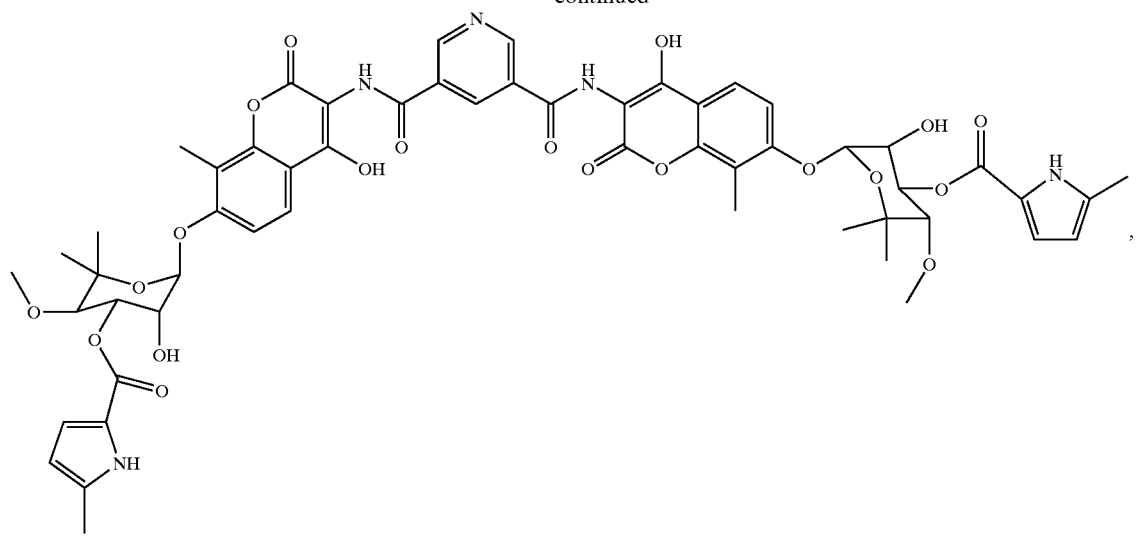
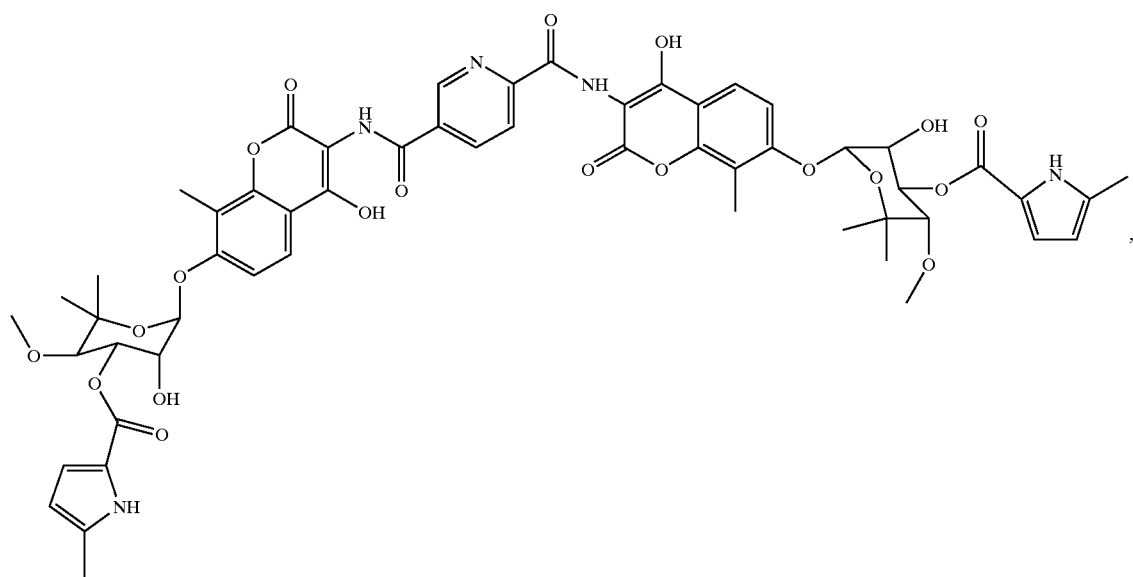
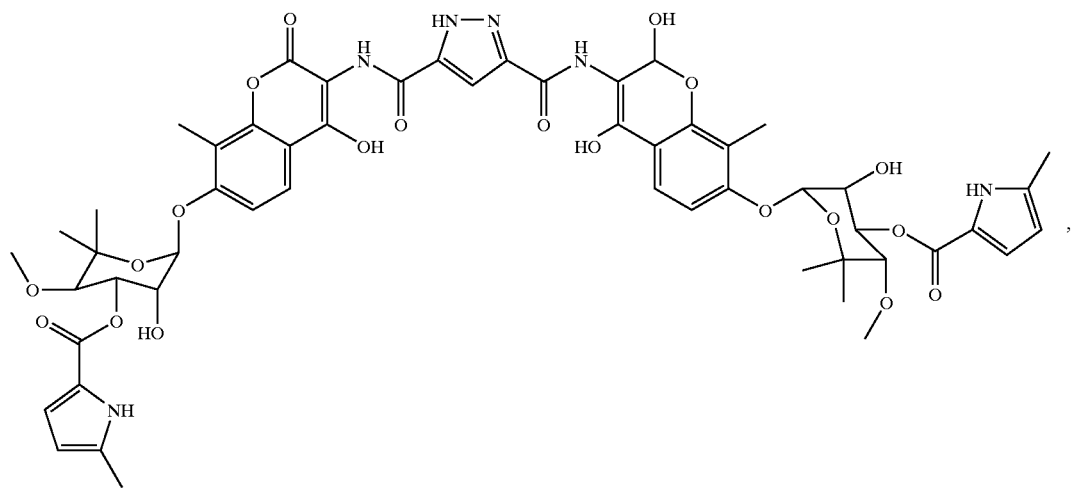

-continued
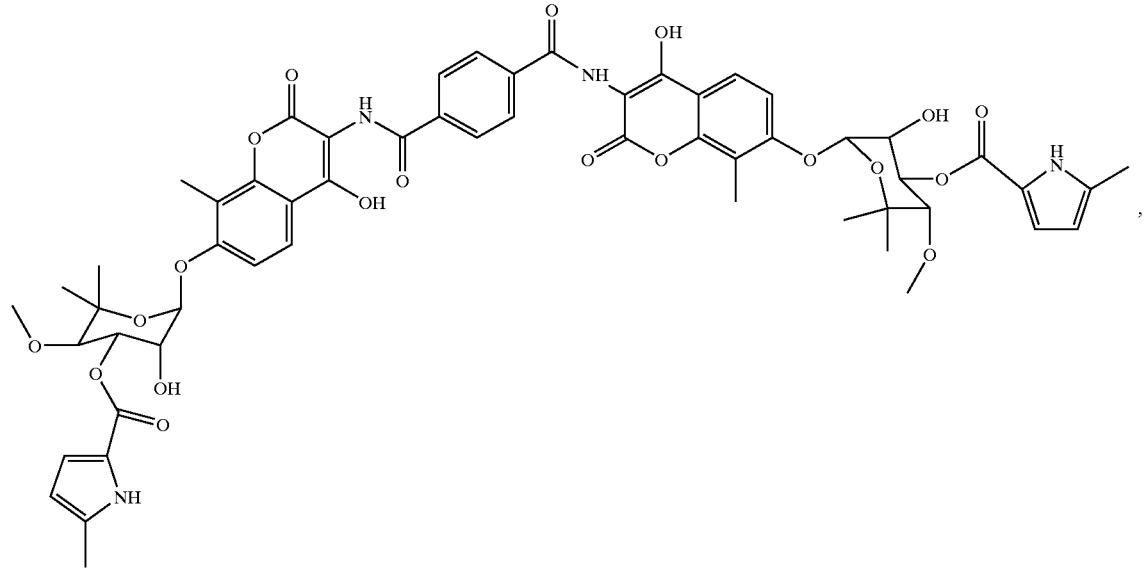
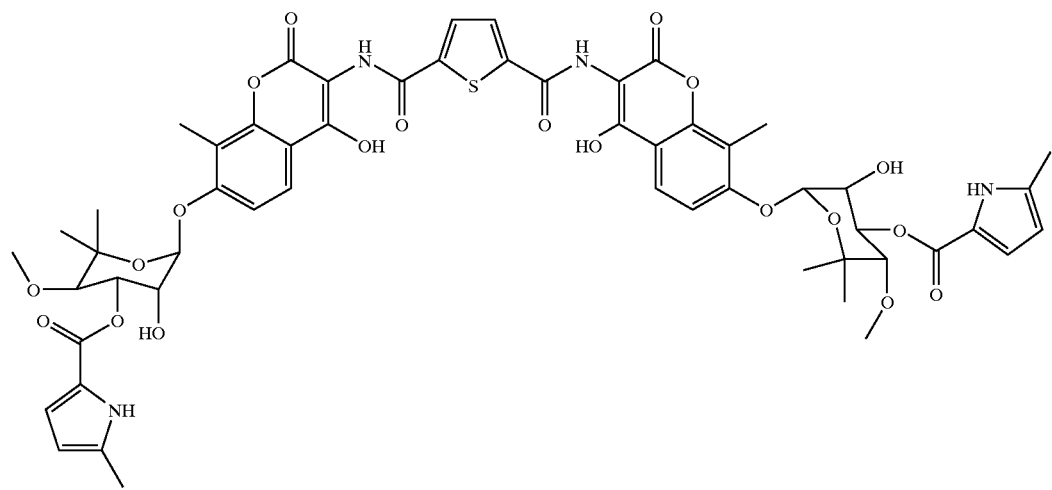
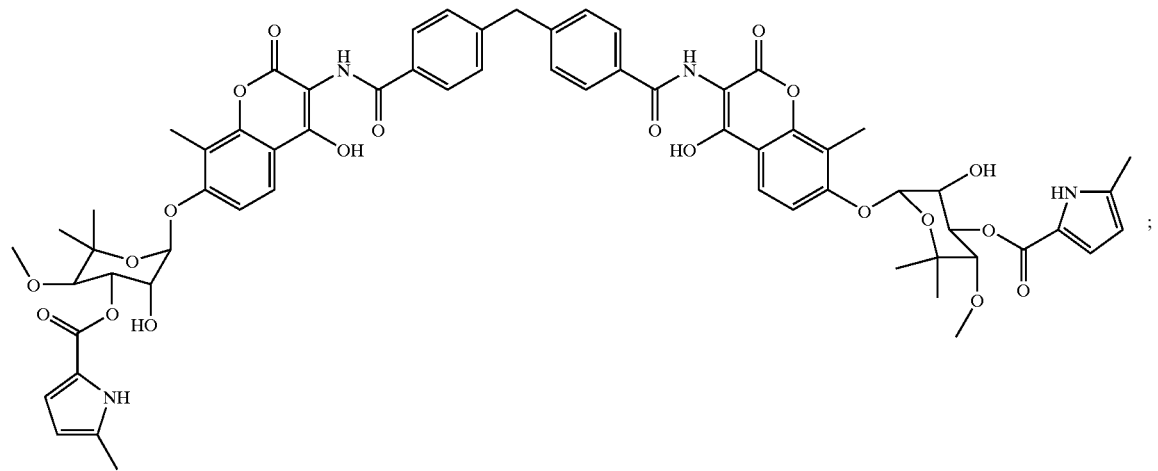

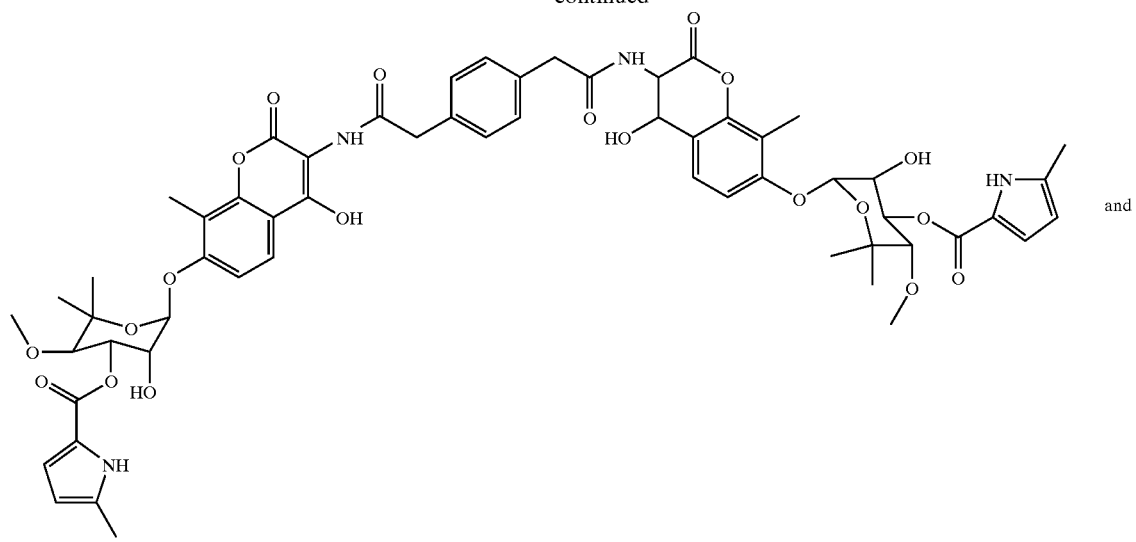
and
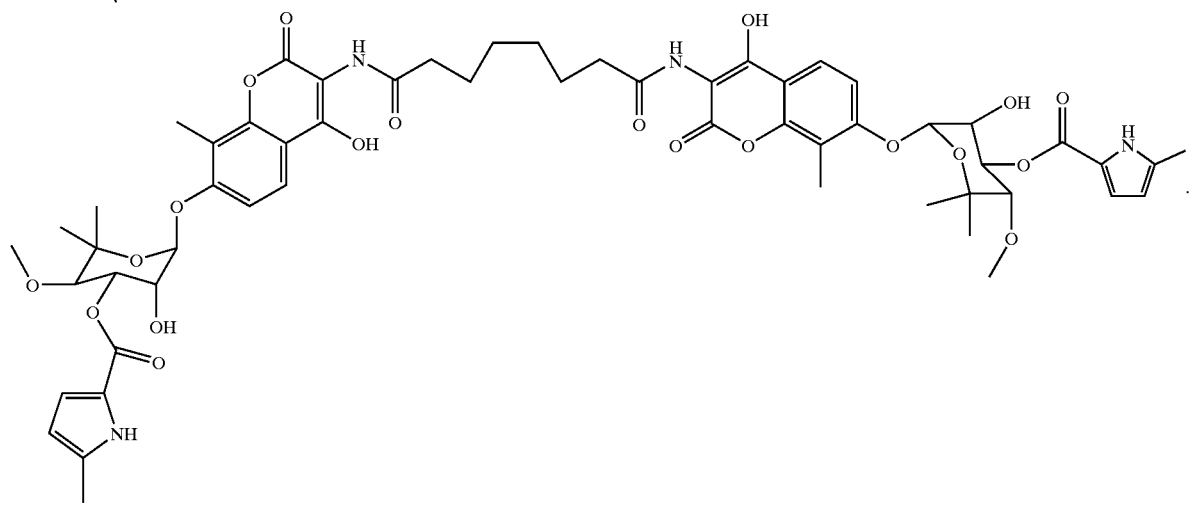
14. A method of promoting the dimerization of chimeric signaling, intracellular proteins comprising contacting a cell containing said proteins with a compound of formula I:
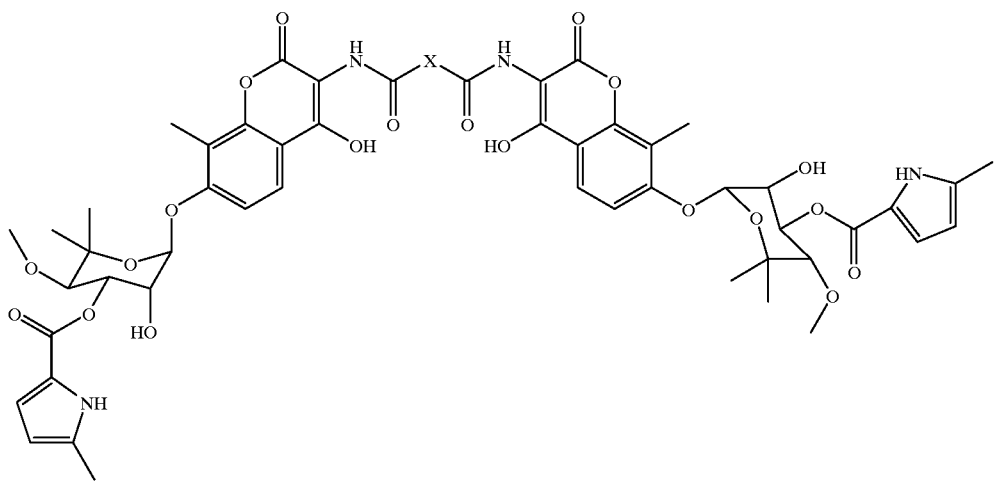

or a pharmaceutically acceptable salt or ester thereof,
wherein X is a linking group X is selected from the group consisting of straight, branched and cyclic alkyl, aryl, diaryl, heteroaryl, said alkyl, aryl, diaryl and heteroaryl optionally substituted with 1–3 groups of $C_{1-6}$ alkyl or $NH_2$, alkyl with 1–3 heteroatoms in the chain, and a combination of alkyl, aryl and/or heteroaryl substituents, provided that when X is a substituted heteroaryl it is not

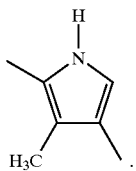

15. A method according to claim 14 wherein X is selected from the group consisting of pyridine, furan, indole, benzofuran, pyrrole, dibenzofuran, thiophene, straight chain alkyl, cycloalkyl, phenyl, diaryl and combinations thereof.

16. The method according to claim 15, wherein the pyrrolyl moiety is selected from the group consisting of

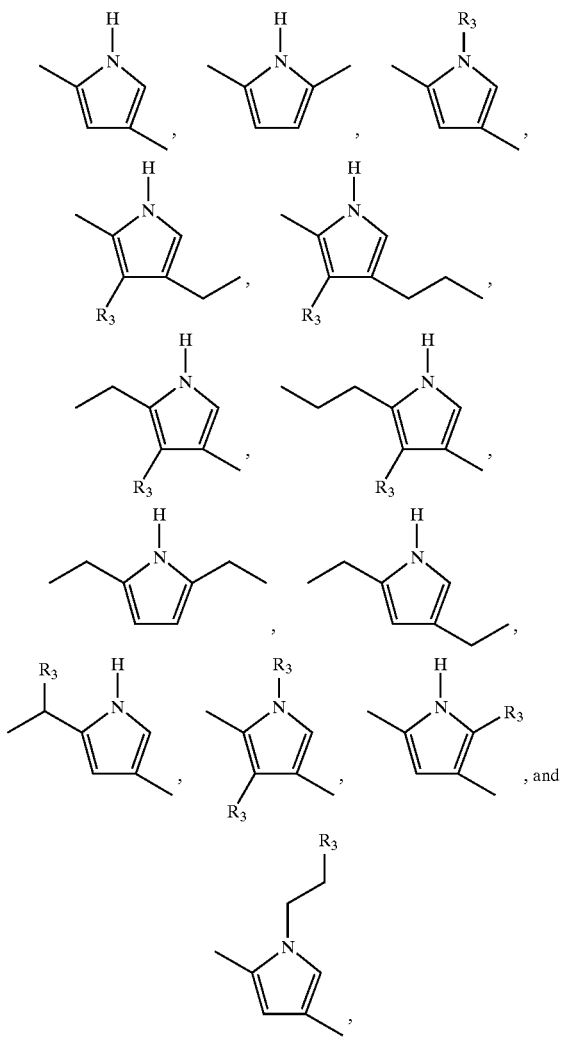

wherein $R_3$ is H or $CH_3$.

17. The method according to claim 15, wherein diaryl is selected from the group consisting of

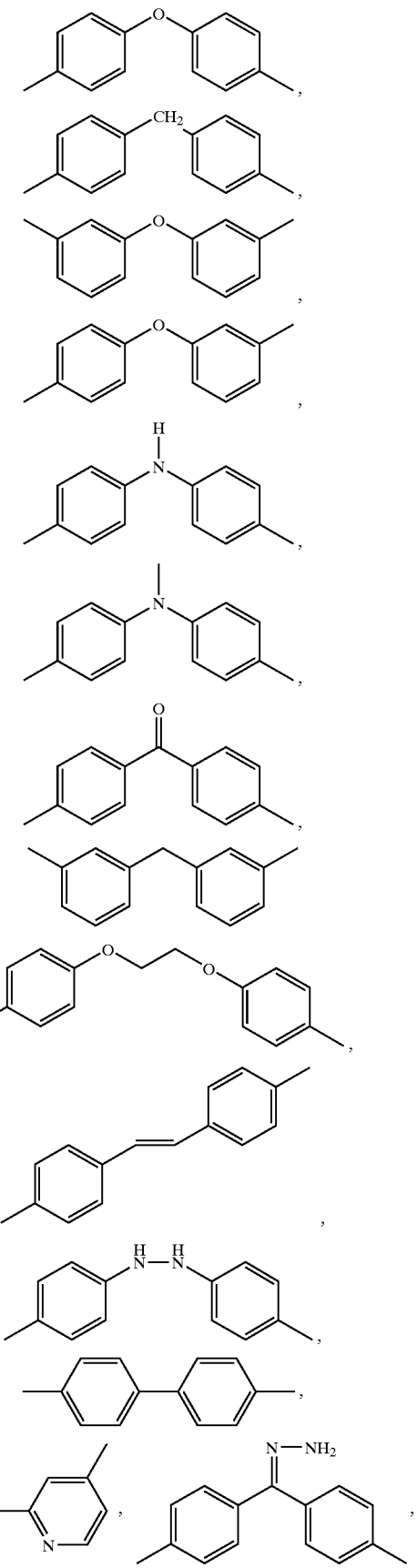

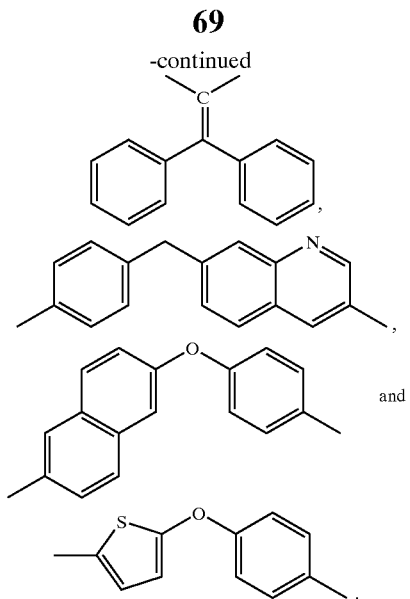

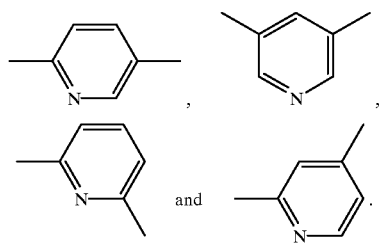

18. The method according to claim 15, wherein pyridine is selected from the group consisting of

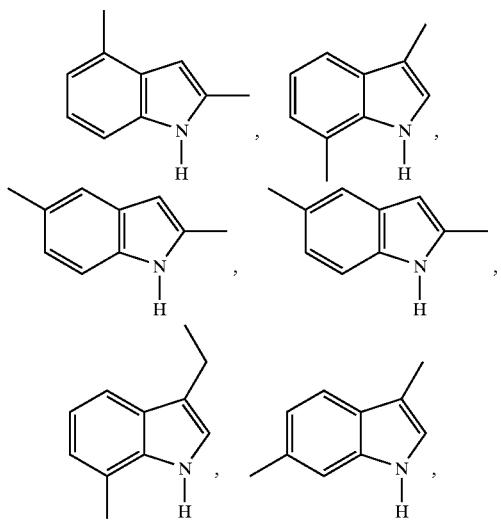

19. The method according to claim 15, wherein the straight chain alkyl contains from one to eighteen carbon atoms.

20. The method according to claim 15, wherein indolyl is selected from the group consisting of

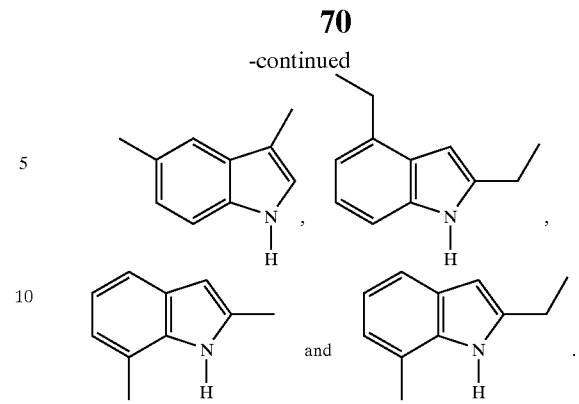

21. The method according to claim 15, wherein benzofuranyl is selected from the group consisting of

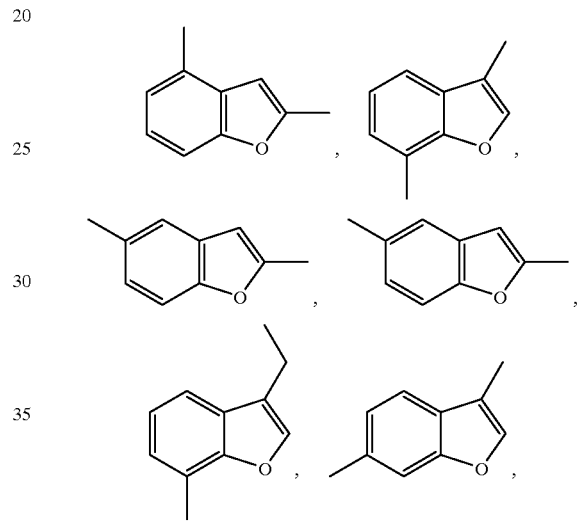

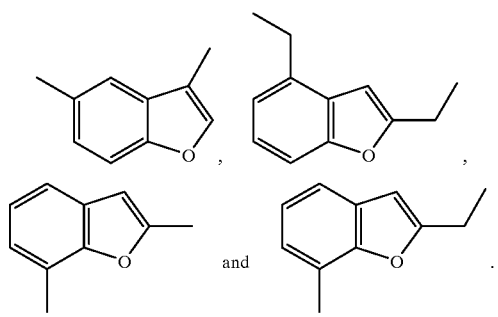

22. The method according to claim 15, wherein phenyl is selected from the group consisting of

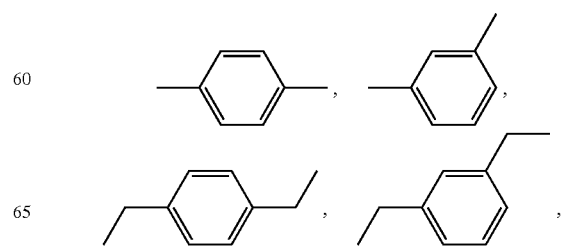

-continued

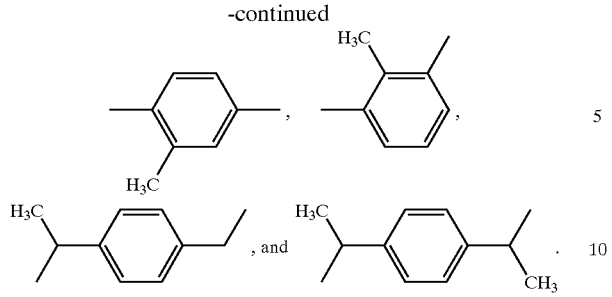

23. The method according to claim 15, wherein cycloalkyl is selected from the group consisting of

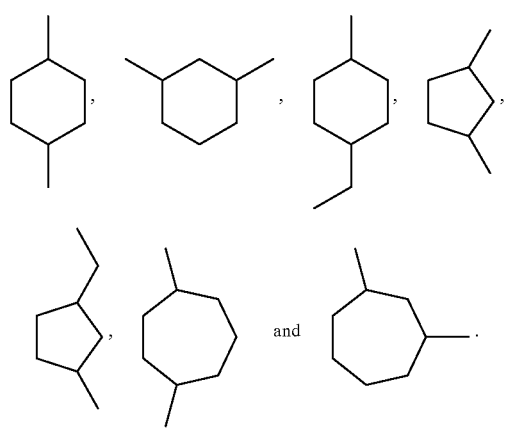

24. The method according to claim 15, wherein furanyl is selected from the group consisting of

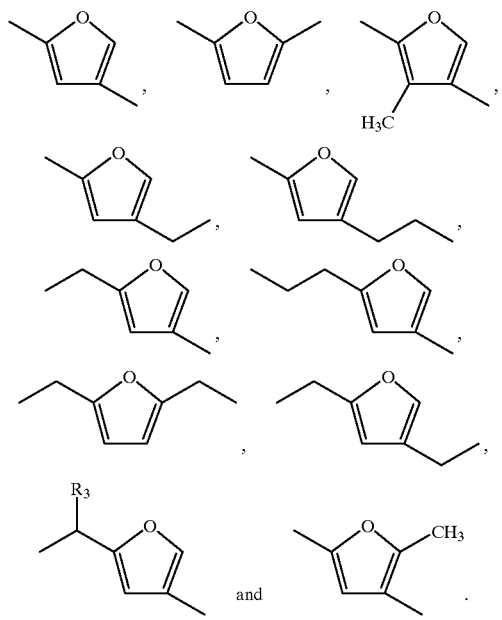

25. The method according to claim 15, wherein dibenzofuranyl is selected from the group consisting of

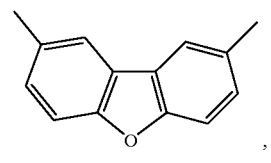

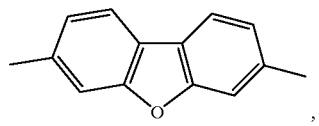

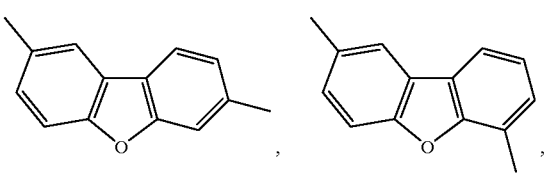

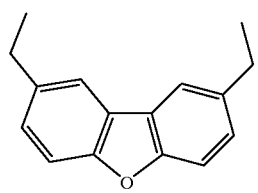

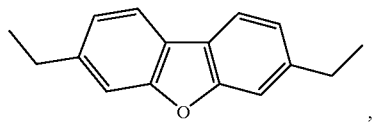

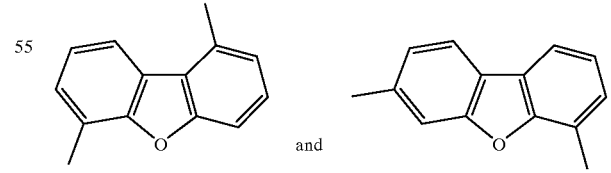

26. A composition useful for promoting the dimerization of chimeric signaling, intracellular proteins comprising a pharmaceutically acceptable carrier and a compound of formula I:

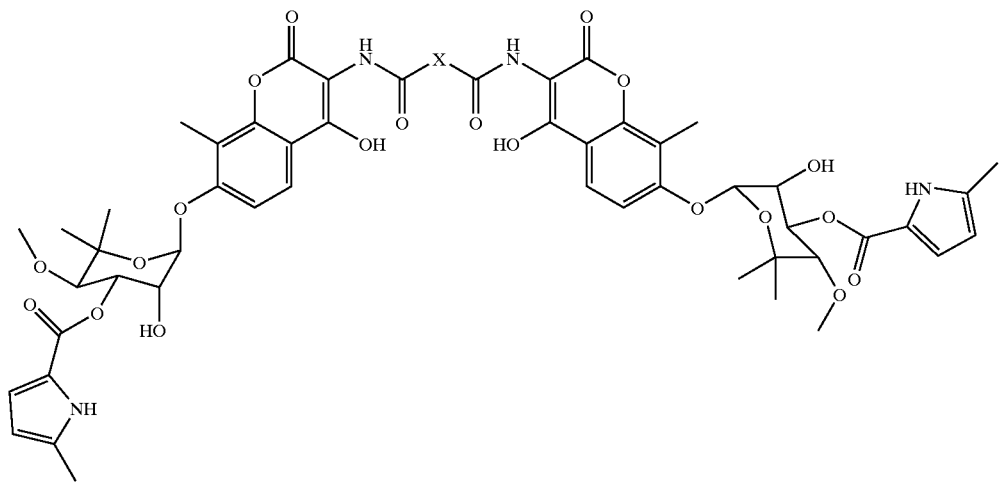

or a pharmaceutically acceptable salt or ester thereof, wherein X is a linking group selected from the group consisting of straight, branched and cyclic alkyl, aryl, diaryl, heteroaryl, said alkyl, aryl, diaryl and heteroaryl optionally substituted with 1–3 groups of $C_{1-6}$ alkyl or $NH_2$, alkyl with 1–3 heteroatoms in the chain, and a combination of alkyl, aryl and/or heteroaryl substituents, provided that when X is a substituted heteroaryl it is not

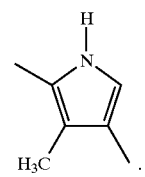

* * * * *